United States Patent
Gasperment et al.

(10) Patent No.: US 11,564,736 B2
(45) Date of Patent: Jan. 31, 2023

(54) SYSTEMS AND METHODS FOR APPLYING ENERGY TO OVARIAN TISSUE

(71) Applicant: May Health SAS, Paris (FR)

(72) Inventors: Marion Gasperment, Paris (FR); Tim Lenihan, Hradek Kralove (CZ); Anne Osdoit, Paris (FR)

(73) Assignee: May Health SAS, Paris (FR)

( * ) Notice: Subject to any disclaimer, the term of this patent is extended or adjusted under 35 U.S.C. 154(b) by 173 days.

(21) Appl. No.: 16/751,148

(22) Filed: Jan. 23, 2020

(65) Prior Publication Data

US 2020/0237437 A1 Jul. 30, 2020

Related U.S. Application Data

(60) Provisional application No. 62/797,191, filed on Jan. 25, 2019.

(51) Int. Cl.
*A61B 18/00* (2006.01)
*A61B 18/14* (2006.01)

(52) U.S. Cl.
CPC ............... *A61B 18/1477* (2013.01); *A61B 2018/00559* (2013.01); *A61B 2018/00577* (2013.01); *A61B 2018/00791* (2013.01); *A61B 2018/00875* (2013.01)

(58) Field of Classification Search
CPC ...... A61B 18/1477; A61B 2018/00559; A61B 2018/00577; A61B 2018/00791; A61B 2018/00875
See application file for complete search history.

(56) References Cited

U.S. PATENT DOCUMENTS

| | | |
|---|---|---|
| 4,838,506 A | 6/1989 | Cooper |
| 4,877,033 A | 10/1989 | Seitz, Jr. |
| 5,366,490 A | 11/1994 | Edwards et al. |
| 5,395,363 A | 3/1995 | Billings et al. |
| 5,540,681 A | 7/1996 | Strul et al. |
| 5,558,673 A | 9/1996 | Edwards et al. |
| 5,810,804 A | 9/1998 | Gough et al. |
| 5,853,368 A | 12/1998 | Solomon et al. |
| 5,868,740 A | 2/1999 | Leveen et al. |
| 5,931,787 A | 8/1999 | Dietz et al. |

(Continued)

FOREIGN PATENT DOCUMENTS

| | | |
|---|---|---|
| CN | 103385754 A | 11/2013 |
| CN | 103458968 A | 12/2013 |

(Continued)

OTHER PUBLICATIONS

Amer et al., Ovulation Induction Using Laparoscopic Ovarian Drilling in Women with Polycystic Ovarian Syndrome: Predictors of Success, Human Reproduction, vol. 19(8):1719-1724 (2004).

(Continued)

*Primary Examiner* — Joanne M Hoffman
*Assistant Examiner* — Rachel A. Vierra
(74) *Attorney, Agent, or Firm* — Eversheds Sutherland (US) LLP; Christopher C. Bolten; Albert K. Heng

(57) ABSTRACT

Described herein are methods and systems for performing a procedure for ovarian rebalancing. The methods and systems may be used in the treatment of polycystic ovary syndrome (PCOS). The systems and methods may also be useful in the treatment of infertility associated with PCOS.

26 Claims, 22 Drawing Sheets

(56) References Cited

U.S. PATENT DOCUMENTS

| | | | |
|---|---|---|---|
| 5,979,453 A | 11/1999 | Savage et al. | |
| 6,063,078 A | 5/2000 | Wittkampf | |
| 6,095,981 A | 8/2000 | McGahan et al. | |
| 6,165,173 A | 12/2000 | Kamdar et al. | |
| 6,200,313 B1 | 3/2001 | Abe et al. | |
| 6,254,601 B1 | 7/2001 | Burbank et al. | |
| 6,368,280 B1 | 4/2002 | Cermak et al. | |
| 6,425,867 B1 | 7/2002 | Vaezy et al. | |
| 6,575,969 B1* | 6/2003 | Rittman, III | A61B 18/1482 606/41 |
| 6,602,251 B2 | 8/2003 | Burbank et al. | |
| 6,716,184 B2 | 4/2004 | Vaezy et al. | |
| 6,764,488 B1 | 7/2004 | Burbank et al. | |
| 6,884,219 B1 | 4/2005 | Pruter | |
| 6,936,048 B2 | 8/2005 | Hurst | |
| 7,676,269 B2 | 3/2010 | Yun et al. | |
| 7,691,086 B2 | 4/2010 | Tkebuchava | |
| 7,771,357 B2 | 8/2010 | Burbank et al. | |
| 7,815,571 B2 | 10/2010 | Deckman et al. | |
| 7,874,986 B2 | 1/2011 | Deckman et al. | |
| 7,918,795 B2 | 4/2011 | Grossman | |
| 7,981,041 B2 | 7/2011 | McGahan | |
| 8,025,656 B2 | 9/2011 | Gruber et al. | |
| 8,080,009 B2 | 12/2011 | Lee et al. | |
| 8,088,072 B2 | 1/2012 | Munrow et al. | |
| 8,121,690 B2 | 2/2012 | Yun et al. | |
| 8,206,300 B2 | 6/2012 | Deckman et al. | |
| 8,262,574 B2 | 9/2012 | Placek et al. | |
| 8,262,577 B2 | 9/2012 | Munrow et al. | |
| 8,298,145 B2 | 10/2012 | Deckman et al. | |
| 8,444,636 B2 | 5/2013 | Shadduck et al. | |
| 8,506,485 B2 | 8/2013 | Deckman et al. | |
| 8,512,330 B2 | 8/2013 | Epstein et al. | |
| 8,512,333 B2 | 8/2013 | Epstein et al. | |
| 8,528,563 B2 | 9/2013 | Gruber | |
| 8,992,427 B2 | 3/2015 | Munrow et al. | |
| 9,357,977 B2 | 6/2016 | Grossman | |
| 9,510,898 B2 | 12/2016 | Epstein et al. | |
| 9,517,047 B2 | 12/2016 | Grossman | |
| 9,662,166 B2 | 5/2017 | Lee et al. | |
| 9,750,568 B2 | 9/2017 | Sobotka et al. | |
| 9,861,336 B2 | 1/2018 | Munrow et al. | |
| 9,861,426 B2 | 1/2018 | Epstein et al. | |
| 10,595,936 B2 | 3/2020 | Zarins et al. | |
| 2002/0013571 A1 | 1/2002 | Goldfarb et al. | |
| 2002/0120238 A1 | 8/2002 | McGuckin, Jr. et al. | |
| 2003/0028111 A1 | 2/2003 | Vaezy et al. | |
| 2003/0069572 A1 | 4/2003 | Wellman et al. | |
| 2003/0130575 A1 | 7/2003 | Desai | |
| 2003/0130598 A1* | 7/2003 | Manning | A61B 5/6852 600/585 |
| 2004/0143252 A1 | 7/2004 | Hurst | |
| 2004/0162554 A1* | 8/2004 | Lee | A61B 18/14 606/45 |
| 2005/0059964 A1 | 3/2005 | Fitz | |
| 2005/0090741 A1 | 4/2005 | Kisen et al. | |
| 2005/0203399 A1 | 9/2005 | Vaezy et al. | |
| 2006/0178665 A1 | 8/2006 | Sloan et al. | |
| 2006/0189972 A1 | 8/2006 | Grossman | |
| 2007/0161905 A1 | 7/2007 | Munrow | |
| 2007/0179380 A1 | 8/2007 | Grossman | |
| 2007/0249936 A1 | 10/2007 | Deckman et al. | |
| 2008/0167649 A1 | 7/2008 | Edwards et al. | |
| 2008/0245371 A1 | 10/2008 | Gruber | |
| 2009/0118727 A1 | 5/2009 | Pearson et al. | |
| 2009/0131790 A1 | 5/2009 | Munrow et al. | |
| 2009/0171304 A1* | 7/2009 | Cao | A61B 17/3478 604/272 |
| 2010/0069899 A1 | 3/2010 | Lonero et al. | |
| 2010/0121319 A1 | 5/2010 | Chu et al. | |
| 2010/0145325 A1 | 6/2010 | Hoey et al. | |
| 2010/0168713 A1 | 7/2010 | Tkebuchava | |
| 2010/0222668 A1 | 9/2010 | Dalke et al. | |
| 2011/0077628 A1 | 3/2011 | Hoey et al. | |
| 2011/0087100 A1 | 4/2011 | Grossman | |
| 2011/0144468 A1 | 6/2011 | Boggs et al. | |
| 2011/0288412 A1 | 11/2011 | Deckman et al. | |
| 2011/0288540 A1 | 11/2011 | Wright et al. | |
| 2012/0035474 A1 | 2/2012 | Deckman et al. | |
| 2012/0310236 A1 | 12/2012 | Placek et al. | |
| 2012/0316440 A1 | 12/2012 | Munrow et al. | |
| 2013/0096431 A1 | 4/2013 | Vaezy et al. | |
| 2013/0137979 A1 | 5/2013 | Deckman et al. | |
| 2013/0144283 A1 | 6/2013 | Barman | |
| 2013/0296699 A1 | 11/2013 | Deckman et al. | |
| 2013/0325052 A1 | 12/2013 | Chang et al. | |
| 2014/0073910 A1 | 3/2014 | Munrow et al. | |
| 2015/0051594 A1* | 2/2015 | Sobotka | A61B 18/1492 606/21 |
| 2015/0133911 A1* | 5/2015 | Batchelor | A61B 18/1206 606/34 |
| 2016/0025055 A1 | 1/2016 | Aleker et al. | |
| 2016/0113621 A1 | 4/2016 | Deckman et al. | |
| 2016/0220302 A1* | 8/2016 | Zarins | A61B 8/0841 |
| 2016/0338628 A1* | 11/2016 | Shah | A61M 5/3286 |
| 2017/0065334 A1* | 3/2017 | Wright | A61B 18/1477 |
| 2017/0215949 A1 | 8/2017 | Zarins et al. | |
| 2017/0245838 A1 | 8/2017 | Munrow et al. | |
| 2017/0245891 A1 | 8/2017 | Munrow et al. | |
| 2017/0333116 A1 | 11/2017 | Lee et al. | |
| 2018/0110554 A1 | 4/2018 | Zarins et al. | |
| 2018/0116630 A1 | 5/2018 | Dykes et al. | |
| 2018/0318026 A1 | 11/2018 | Placek et al. | |

FOREIGN PATENT DOCUMENTS

| | | |
|---|---|---|
| CN | 207245117 U | 4/2018 |
| EP | 1 139 899 B1 | 8/2006 |
| EP | 1 967 147 A2 | 9/2008 |
| EP | 1 971 266 A2 | 9/2008 |
| EP | 1 971 267 A2 | 9/2008 |
| EP | 2 007 284 A2 | 12/2008 |
| EP | 1 583 479 B1 | 3/2009 |
| EP | 2 150 180 A1 | 2/2010 |
| EP | 2 209 423 A1 | 7/2010 |
| EP | 2 328 479 A1 | 6/2011 |
| EP | 2 400 910 B1 | 6/2015 |
| JP | S6343648 A | 2/1988 |
| JP | 2010-118072 A | 5/2010 |
| JP | 63-043648 B2 | 6/2018 |
| WO | WO-9734534 A1 | 9/1997 |
| WO | WO-98/44857 A1 | 10/1998 |
| WO | WO-2010/099481 A1 | 9/2010 |
| WO | WO-2013/093924 A2 | 6/2013 |
| WO | WO-2015/058096 A1 | 4/2015 |
| WO | WO-2016/161011 A1 | 10/2016 |

OTHER PUBLICATIONS

Badawy, M.D., et al., Ultrasound-guided transvaginal ovarian needle drilling (UTND) for treatment of polycystic ovary syndrome: a randomized controlled trial, Fertility and Sterility, 91(4):1164-1167 (2009).

El-Edesy, et al., Harmonic Laparoscopic Ovarian Drilling In Polycystic Ovarian Syndrome, AAMJ 11(3):146-158 (2013).

Extended European Search Report dated Aug. 2, 2017 in EP Patent Appl. Serial No. 14853276.5 (117149-0230).

Fernandez et al., Ovarian Drilling for Surgical Treatment of Polycystic Ovarian Syndrome: A Comprehensive Review; Reproductive BioMedicine Online, 22:556-568 (2011).

Flyckt, M.D., et al., Laparoscopic Ovarian Drilling for Clomiphene-Resistant Polycystic Ovary Syndrome, Seminars In Reproductive Medicine, vol. 29(2):138-146 (2011).

Hashim et al., Three Decades After Gjonnaess's Laparoscopic Ovarian Drilling for Treatment of PCOS; What Do We Know?, An Evidence-Based Approach, Arch Gynecol. Obstet., 288:409-422 (2013).

Hendriks et al., Extensive tissue damage of bovine ovaries after bipolar ovarian drilling compared to monopolar electrocoagulation or carbon dioxide laser, Fertility and Sterility, 93:2 (2010).

(56) References Cited

OTHER PUBLICATIONS

International Search Report & Written Opinion dated Mar. 26, 2015 in Int'l PCT Patent Appl. Serial No. PCT/US14/61159 (117149-0210).
International Search Report & Written Opinion dated Jul. 26, 2016 in Int'l PCT Patent Application Serial No. PCT/US2016/025055 (117149-0310).
Moussatov, et al., A Possible Approach To The Treatment of Polycystic Ovarian Syndrome Using Focused Ultrasound, Ultrasonics, 36(8):893-900 (1998).
Pimentel, et al., Adequacy of ovarian diathermy under ultrasound control: an experimental model, Journal of Ovarian Research, 6:54 (2013).
Supplementary European Search Report dated Dec. 12, 2018 in EP Patent Appl. Serial No. 16774124.8 (117149-0330).
Syritsa, A., Transvaginal Ultrasound-Guided Electrocautery of the Ovaries in Infertile Patients With Polycystic Ovarian Disease, Int'l J. Gynecology Obstetrics 63:293-294 (1998).
U.S. Appl. No. 15/094,852, filed Apr. 8, 2016.
U.S. Appl. No. 15/494,188, filed Apr. 21, 2017.
U.S. Appl. No. 15/562,861, filed Sep. 28, 2017.
Communication Relating to the Results of the Partial International Search dated May 26, 2020 in Int'l PCT Patent Appl. Serial No. PCT/162020/050546 (0410-PCT).
Extended European Search Report dated May 12, 2020 in EP Patent Appl. Serial No. 20157223.7 (0235).

\* cited by examiner

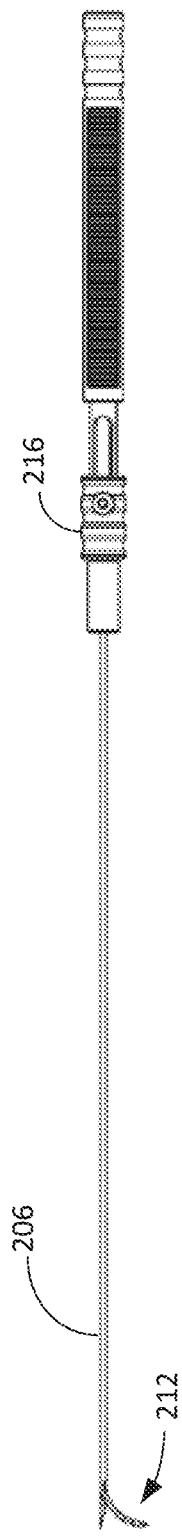
FIG. 2G
FIG. 2H

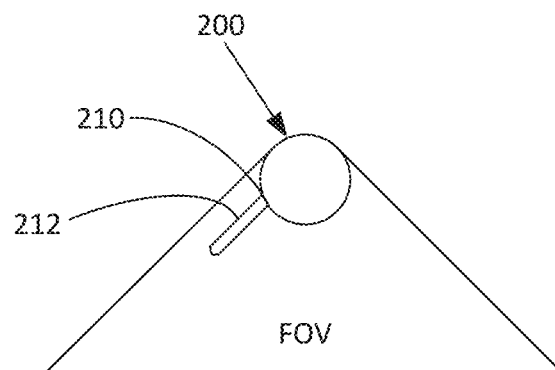
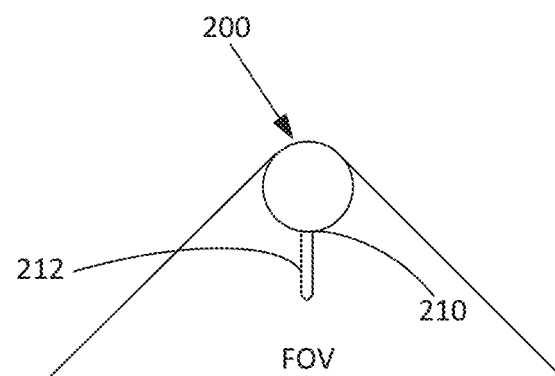
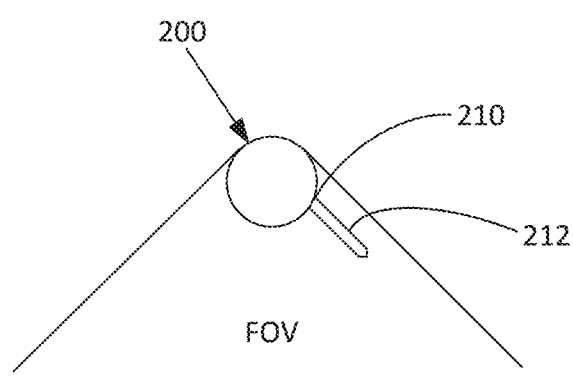
FIG. 3C

Ablation Parameter Selection

Ovarian Volume 10.4 cm³

| Ablation Volume | 4 Ablations | 5 Ablations | 6 Ablations | 7 Ablations | 8 Ablations |
|---|---|---|---|---|---|
| 5.0% | 60 sec 85 °C | 48 sec 85 °C | 40 sec 85 °C | 34 sec 85 °C | 30 sec 85 °C |
| 7.5% | 90 sec 85 °C | 72 sec 85 °C | 60 sec 85 °C | 51 sec 85 °C | 45 sec 85 °C |
| 10.0% | 120 sec 85 °C | 96 sec 85 °C | 80 sec 85 °C | 68 sec 85 °C | 60 sec 85 °C |

FIG. 13

SYSTEMS AND METHODS FOR APPLYING ENERGY TO OVARIAN TISSUE

CROSS-REFERENCE TO RELATED APPLICATIONS

This application claims the benefit of priority of U.S. Provisional Patent Application No. 62/797,191, filed Jan. 25, 2019, the entire contents of which are incorporated herein by reference.

FIELD OF THE INVENTION

Described herein are systems and methods for the manipulation of ovarian tissues. The systems and methods may be used in the treatment of polycystic ovary syndrome (PCOS), infertility, and/or other diseases/disorders involving the ovaries, or for modulating ovulation.

BACKGROUND

In instances of disease in the ovaries and/or in the case of certain types of infertility, there may be a need to manipulate ovarian tissues, retrieve tissues, or deliver agents within a patient's ovaries. For some time, physicians have used direct surgical access, laparoscopic access, or transvaginal ultrasound-directed needle-based methods for accessing ovaries. Direct surgical access is typically obtained under anesthesia and involves a skin incision to directly expose and operate on the tissue. Laparoscopic access is typically obtained under anesthesia, involves two or more skin incisions, and further entails inflating the space surrounding the ovaries with either gas or fluid and using a camera and laparoscopic tools to visualize and operate on the tissue. Transvaginal ultrasound-directed needle-based access is often employed for oocyte retrieval as a part of in vitro fertilization (IVF). These current approaches have some limitations: the surgical and laparoscopic access methods are generally more invasive and thus require more anesthesia and a higher acuity of care. Moreover, the surgical and laparoscopic access methods allow for direct visualization of the surface of the ovaries, but they provide less ability to visualize where a specific device is deployed within the tissue of the ovary. Because transvaginal needle access is typically performed under ultrasound, it allows for delivery of the tip of the needle into specific locations within the ovary, and these can be visualized in real-time; current systems however are limited because the needles used to access the tissue are only single or dual lumen needles and are not able to do more than simply aspirate. Current systems are not ideally suited for the instance where it would be desirable to either deliver or remove specific tissue or other factors from the ovaries via the transvaginal ultrasound guided needle route. Current systems are also not ideally suited for delivery of specific agents or energy to ovaries.

Manipulation of ovarian tissues may be to treat Polycystic Ovary Syndrome (PCOS). PCOS is an endocrine disorder that was initially characterized in the 1930s by Stein & Leventhal. Features of the syndrome may include: oligo/amenorrhea, oligo/anovulation, hirsutism, acne, obesity, and characteristic polycystic appearance of the ovaries. PCOS generally has significant effects on reproductive health (e.g., oligo/amenorrhea and oligo/anovulation, bleeding, endometrial hyperplasia, infertility, and increased risk of endometrial cancers) as well as non-reproductive health (e.g., hyperandrogenism, carcinoma, insulin resistance, hypercholesterolemia, hypertension, obesity, sleep apnea, and cardiovascular disease). PCOS has historically been considered in the context of hormonal dysregulation characterized by alterations in gonadotropin secretion, increased androgen production, increased insulin resistance, increased cortisol production, and obesity. It has also been shown that PCOS is often accompanied by increased activity of the sympathetic nervous system.

Treatment of PCOS can be costly to the health care system. Key non-infertility treatments include: oral contraceptives (for hormonal normalization), endometrial ablation (for anovulatory bleeding), insulin sensitizing agents, antihypertensive agents, statins, and treatments for severe acne and hirsutism.

Many women with PCOS may also require infertility treatment during their lifetime. Treatment for PCOS infertility typically follows a step-wise approach. For example, letrozole and/or clomiphene citrate is generally the first-line treatment with second-line treatment being either gonadotropin administration or ovarian drilling (also sometimes referred to as ovarian diathermy). If these treatments are unsuccessful, in vitro fertilization (IVF) is attempted. However, multiple pregnancies and live births (e.g., twins) are common with clomiphene citrate, gonadotropin, and IVF treatments. In infertility treatment, multiple pregnancies and live births is often considered an undesirable result due to the associated perinatal and neonatal morbidity and the associated elevated costs. Furthermore, ovarian hyperstimulation syndrome (OHSS) may be more common in women with PCOS undergoing gonadotropin or IVF treatment. While OHSS is often mild and easily treated, more severe cases may require aggressive treatment.

Alternatively, ovarian drilling may be an option in treating PCOS, PCOS-associated symptoms/disorders, and PCOS related infertility. Prior to the development of ovarian drilling, other types of surgery were performed on the ovaries for the treatment of infertility. Ovarian wedge resection, a well-established procedure first described in the late 1940s, involves surgically removing wedge-shaped pieces of ovarian tissue from polycystic ovaries. Despite the effectiveness of the procedure, ovarian wedge resection has generally been abandoned in favor of new techniques because of the frequent occurrence of adhesions with the technique. Other ovarian surgeries for infertility in PCOS that have been performed are ovarian electrocautery, ovarian laser vaporization, multiple ovarian biopsies, and others.

Ovarian drilling/diathermy (OD) was developed in the 1970s and 1980s by Gjönnaess. Recently, OD has been the most frequently described ovarian surgery for infertility in women with PCOS. In this laparoscopic procedure, radiofrequency energy, or other techniques, is used to bore multiple holes in the ovary. There are common findings following the surgery including acute changes in ovarian and pituitary hormones followed by a prolonged reduction of circulating androgens. In randomized trials, rates of pregnancy and live birth have been shown to be similar to those associated with gonadotropin treatment, but with significantly reduced rates of multiple pregnancies while benefiting from a one-time treatment, enabling a natural pregnancy experience.

Despite this evidence, ovarian drilling is not used as frequently in clinical practice as other treatments for PCOS infertility. This may be due to: (1) the lack of standardized, consistent methods of targeting and performing surgeries on the ovary; (2) the invasive nature of current OD technologies; (3) the theoretical risk of adhesions from intervention on the ovaries; (4) the surgical route of access is not a good fit for the clinical practice patterns of fertility physicians;

and (5) the uncertainty of the mechanism of action. Accordingly, it would be useful to have systems and methods that overcome the limitations of current surgical procedures. Such systems may be designed to consistently target ovarian tissues, reduce the level of invasiveness of the procedure, reduce the risk of adhesions, and enhance positioning in the ovary for targeting non-specific tissue types to treat the disease. Moreover, given that the ovaries or elements therein may play an important role in governing other female health issues such as timing of menopause, hot-flushes, fibroids, hormonal dysregulation, endometriosis, adnexal pain, risk of endometrial cancer, disturbances in glucose metabolism, or cardiovascular health, it would be beneficial to have improved methods and systems for treating these conditions as well as targeting of structures within or nearby the ovaries that may enable treatment of these conditions.

U.S. Patent Publication Nos. 2016/0220302, 2017/0215949, and 2018/0110554 to Zairns, the entire contents of each of which are incorporated herein by reference, describe improved systems and methods for manipulating ovarian tissue.

SUMMARY

Described herein are systems and methods for performing an ovarian procedure called ovarian rebalancing. The manipulation of ovarian tissues may include delivering/applying energy; e.g., radiofrequency energy, microwave energy, cryoablative energy, unfocused or focused ultrasound; for ovarian rebalancing. In other variations, the manipulation of ovarian tissues may include retrieving tissues, e.g., via aspiration, or delivering agents within a patient's ovaries. In general, the systems and methods are designed to access ovarian tissue or a target region proximate the ovarian tissue transvaginally, laparoscopically, percutaneously, via a natural orifice route through the vagina-uterus-fallopian tubes, through an open surgical approach or via an entirely non-invasive approach. The emission of energy into ovarian tissue (e.g., stroma) ablates the tissue to rebalance the ovary. For example, the ablation(s) is(are) expected to reduce hormonal imbalance between hormones such as the Follicle Stimulating Hormone (FSH) and the Luteinizing Hormone (LH), thereby treating a fertility condition such as Polycystic Ovary Syndrome (PCOS).

Exemplary ovarian tissues include without limitation, the ovaries (e.g., medulla/stroma and/or cortex), ovarian follicles/cysts, nerves associated with the ovaries, suspensory ligaments, ovarian ligaments, broad ligaments, the mesovarium, endometrial tissue within the ovary, tumor or neoplastic cells, or a combination thereof. Stromal tissue generally comprises the middle or medullary region of the ovary. The cortex (or outer region) of the ovary is generally where follicles of different degrees of maturity tend to reside. The term "follicle" includes the oocyte that is contained within the follicle, and may refer to the entire follicular structure or the oocyte specifically. These follicles are sometimes called "cysts" in the setting of PCOS. In other settings, cysts may refer to a collection of fluid that may or may not be a follicle. The methods and systems may be used to rebalance the ovary(ies) to modulate ovulation, treat one or more symptoms of, or disorders associated with, polycystic ovary syndrome, including infertility, or treat other diseases/disorders involving the ovaries.

The system for performing an ovarian procedure, as described herein, may be capable of being advanced proximate to or within an ovary, and in the case of PCOS, an ovarian follicle/cyst or other target tissue (e.g., stroma). In addition, the system may be used with an ultrasound probe. In accordance with one aspect of the present invention, the ultrasound probe may be a vaginal ultrasound probe. According to an exemplary embodiment, systems for performing an ovarian procedure include a therapeutic needle assembly having a proximal region and a distal region. The therapeutic needle assembly includes an elongated shaft at the distal region. The elongated shaft has a lumen, a port, and a needle tip at a distal end of the elongated shaft, the needle tip structured to pierce a vaginal wall and pierce an ovarian wall for placement of the port into an ovary. For example, the needle tip may be cored to define a cavity to facilitate piercing the vaginal wall and the ovarian wall.

The therapeutic needle assembly further includes a therapeutic portion disposed within the lumen of the elongated shaft in a retracted state, the therapeutic portion having an energy emitter that may be deployed to extend out the port of the elongated shaft in a deployed state and to emit energy into ovarian tissue of the ovary while in the deployed state. The therapeutic portion may form a curve in the deployed state, and may include one or more electrodes for emitting the energy into the ovarian tissue. For example, the therapeutic portion further may include an active electrode and a return electrode, and the active electrode may emit continuous or pulsed radiofrequency energy. The therapeutic portion may emit the energy into the ovarian tissue to treat polycystic ovary syndrome (PCOS).

In addition, the therapeutic needle assembly may include a handle at the proximal region, the handle having an actuator for transitioning the therapeutic portion between the retracted state and the deployed state when actuated. In accordance with one aspect, the actuator includes a trigger to release or engage a locking mechanism which aids in deployment of the therapeutic portion. The therapeutic portion may include an echogenic material or region (e.g. air/gas) to enhance visibility. The therapeutic needle assembly, therapeutic portion, and other components, may be made from polymeric materials (e.g., PEEK, polyester, ABS, nylon), metals (e.g., stainless steel), metal alloys (e.g., platinum-iridium), and shape memory materials (e.g., nitinol, elgiloy) all of which are known in the art, and thus are not described in detail here.

Moreover, the elongated shaft is structured to facilitate transitioning of the therapeutic portion between the retracted state and the deployed state responsive to actuation at the actuator without damaging the energy emitter. For example, the system may include a lubricant disposed within the lumen of the elongated shaft adjacent to the port of the elongated shaft for facilitating the transition of the therapeutic portion between the retracted state and the deployed state responsive to actuation at the actuator without damaging the energy emitter. The lubricant may be, e.g., a lubricious tube or coating. Additionally or alternative, the elongated shaft may include a structure or configuration, such as a ramp or radiused curve, to facilitate transitioning of the therapeutic portion between the retracted state and the deployed state.

In addition, the system further may include an adapter having a needle assembly interface and an ultrasound probe interface. The ultrasound probe interface is structured to be removably coupled to the ultrasound probe, and the needle assembly interface is structured to be removably coupled to an adapter interface, which may be part of the handle, such that the therapeutic needle assembly may be coupled to the ultrasound probe. Accordingly, the adapter may longitudinally align the therapeutic needle assembly with the ultrasound probe. In addition, the adapter ensures alignment of the therapeutic portion within a field-of-view of the ultrasound probe. The system further may include a needle guide removably coupled to the ultrasound probe for receiving the elongated shaft therethrough to stabilize the elongated shaft during a procedure. In accordance with one aspect of the present invention, at least one of the therapeutic needle assembly and the needle guide or the needle guide and the adapter may be formed as a single entity.

The adapter interface and the needle assembly interface may permit reorientation of the therapeutic needle assembly relative to the adapter between a first orientation and a second orientation. For example, the adapter interface and the needle assembly interface may lock together in the first orientation and may be detached from one another to permit reorientation of the therapeutic needle assembly relative to the adapter such that the adapter interface and the needle assembly interface may lock together in the second orientation. The therapeutic portion in the first orientation in the deployed state may be offset, for example, less than or equal to 180 degrees from the therapeutic portion in the second orientation in the deployed state. The adapter interface and the needle assembly interface may lock together in at least one of the first orientation and the second orientation. For example, the adapter interface may include first and second notches on opposing surfaces of the handle, the first and second notches structured to contact opposing surfaces of the needle assembly interface to lock the adapter interface to the needle assembly interface in the first orientation and the second orientation. Moreover, the first and second notches or the opposing surfaces of the needle assembly interface, or both, may include a plurality of ribs to enhance locking. In accordance with another aspect of the present invention, the adapter interface and the needle assembly interface may lock together in the first orientation, and permit rotation of the therapeutic needle assembly relative to the adapter such that the adapter interface and the needle assembly interface may lock together in the second orientation. In accordance with another aspect of the present invention, the adapter interface and the needle assembly interface may permit reorientation of the therapeutic needle assembly relative to the adapter between more orientations than a first orientation and a second orientation, for example, a third orientation or a fourth orientation. Additionally, the adapter interface and the needle assembly interface may lock together at any orientation.

The system further may include a generator operatively coupled to the therapeutic portion for delivering energy to the therapeutic portion in the deployed state such that the therapeutic portion emits the energy into the ovarian tissue of the ovary. The generator may supply continuous or pulsed radiofrequency energy, microwave energy, cryoablative energy, unfocused or focused ultrasound. Accordingly, the therapeutic portion may include at least one sensor for generating data during emission of energy from the therapeutic portion. The at least one sensor may include an impedance sensor and at least one temperature sensor measuring temperature at one or more electrodes or probe temperature or both.

The generator may include a processor in electrical communication with the at least one sensor. For example, the processor may execute instructions stored on a non-transitory computer readable medium to: receive the data from the at least one sensor; determine whether the data is within a predetermined range; and instruct the generator to modify delivery of energy to the therapeutic portion if the data indicates that at least one measured parameter is outside of the predetermined range. The processor further may run a routine to cause generation of an alert on a graphical user interface if the data is above a first predetermined threshold or below a second predetermined threshold. In addition, the system may include a graphical user interface for displaying information indicative of a treatment process based on data from the at least one sensor. For example, the graphical user interface may display information showing temperature and power versus time.

Moreover, the processor further may execute instructions stored on the non-transitory computer readable medium to store information indicative of a number of ablations per ovary or per patient and to cause the graphical user interface to display the information indicative of the number of ablations. In addition, the graphical user interface may display information indicative of at least one of: ovarian volume per ovary, ovarian volume per patient, recommended ablation parameters, set ablation parameters, power settings, recommended number of ablations, required number of ablations, recommended volume of ovarian ablation, required volume of ovarian ablation, number of completed ablation, number of remaining ablations, percentage of ovarian volume ablated, or percentage of ovarian volume remaining to be ablated. The information indicative of recommended or set ablation parameters may be displayed in a table, such as a lookup table. The information displayed may be updated after each ablation. The processor may receive input data indicative of, e.g., ovarian volume, such that the information displayed on the graphical user interface is based at least in part on the input data indicative of ovarian volume. Such information is expected to assist the clinician during a procedure that includes multiple ablations (e.g., 4-8 ablations per ovary, for example based on the individual ovarian volume measured, typically by ultrasound, prior to the ablation procedure).

In accordance with another aspect of the present invention, a method for performing an ovarian procedure is provided. The method includes: advancing a distal region of a therapeutic needle assembly into a vagina; piercing a vaginal wall with a needle tip at a distal end of an elongated shaft of the therapeutic needle assembly; piercing an ovarian wall with the needle tip to position a port of the elongated shaft at a desired location within an ovary; deploying a therapeutic portion from a lumen of the elongated shaft and out the port at a first orientation, the elongated shaft structured to facilitate deployment of the therapeutic portion without damaging an energy emitter of the therapeutic portion; emitting energy into ovarian tissue of the ovary via the energy emitter of the therapeutic portion in the first orientation; retracting the therapeutic portion into the lumen of the elongated shaft; reorienting the therapeutic needle assembly while the port of the elongated shaft remains in the ovary; deploying the therapeutic portion from the lumen of the elongated shaft and out the port at a second orientation; and emitting energy into ovarian tissue of the ovary via the energy emitter of the therapeutic portion in the second orientation.

For example, deploying the therapeutic portion from the lumen of the elongated shaft may include sliding the therapeutic portion through a lubricant within the lumen of the elongated shaft adjacent to the port. As described above, the lubricant facilitates deployment of the therapeutic portion without damaging the energy emitter of the therapeutic portion.

In addition, reorienting the therapeutic needle assembly while the port of the elongated shaft remains in the ovary may include reorienting the therapeutic needle assembly relative to the adapter. For example, reorienting the therapeutic needle assembly relative to the adapter may include: detaching the therapeutic needle assembly from the adapter while the port of the elongated shaft remains in the ovary; rotating the therapeutic needle assembly while the adapter remains in place; and re-attaching the therapeutic needle assembly to the adapter. Alternatively, reorienting the therapeutic needle assembly relative to the adapter may include rotating, advancing, or retracting the therapeutic needle assembly relative to the adapter while the port of the elongated shaft remains in the ovary.

Moreover, the method further may include retracting the therapeutic portion into the lumen of the elongated shaft; moving the elongated shaft proximally in the ovary along a common needle path to a second position; deploying the therapeutic portion from the lumen of the elongated shaft and out the port at the second position; and emitting energy into ovarian tissue of the ovary at the second position via the energy emitter of the therapeutic portion.

For example, the therapeutic needle assembly may be moved along the same needle path (e.g., proximally without adjusting the angle of the needle) via a single entry point for further energy delivery. The therapeutic portion may be redeployed inside the ovary at a proximal or distal location relative to the initial/previous ablation site. In this manner, multiple ablations may be achieved in each ovary, such as 4 ablations in a smaller ovary (as determined by the clinician from ultrasound imaging), 8 ablations in a larger ovary, or sufficient ablations and power levels to achieve the desired volume of ablated ovarian tissue.

These system embodiments may have a variety of effects on therapy. These system embodiments, for example, may allow for a minimally-invasive, transvaginal approach, wherein the ovary would be accessed using the needle. The needle tip may be used to puncture through the vaginal wall and into the ovary under transvaginal image guidance. In some cases, this may allow for a single entry point or fewer entry points into the ovary, reducing the risk of adhesions as compared to surgical and laparoscopic approaches with tissue dissection and entry points for each ablation in the ovary. Once in position in the ovary, the therapeutic portion may be advanced or deployed into the tissue. Here, the releasably securable adapter allows the therapeutic portion to be flipped or rotated (e.g., 60, 90, 120, 180 degrees) so additional regions of the ovary could be accessed and treated without removing the therapeutic needle assembly. The advantages of a transvaginal approach over surgical or laparoscopic approaches generally include one or more of the following: (a) conscious sedation vs. general anesthesia which reduces cost and patient risk, (b) no external scars, (c) less tissue manipulation resulting in lower risk of adhesions, (d) fewer access points into the ovary resulting in lower risk of adhesions, (e) faster recovery time, (f) it is a familiar access route for OB/GYN and fertility physicians, and fits within existing care pathways, and (g) rebalances the ovary(ies) to effectively treat the condition(s).

BRIEF DESCRIPTION OF THE DRAWINGS

FIG. 3C is a front cross-sectional view of the field of view of an ultrasound probe illustrating reorientation of the therapeutic needle assembly within the field of view of the ultrasound transducer in accordance with the principles of the present invention.

FIGS. 10-13 are exemplary snapshots of a graphical user interface generated by the generator software.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION

Figure 1A:
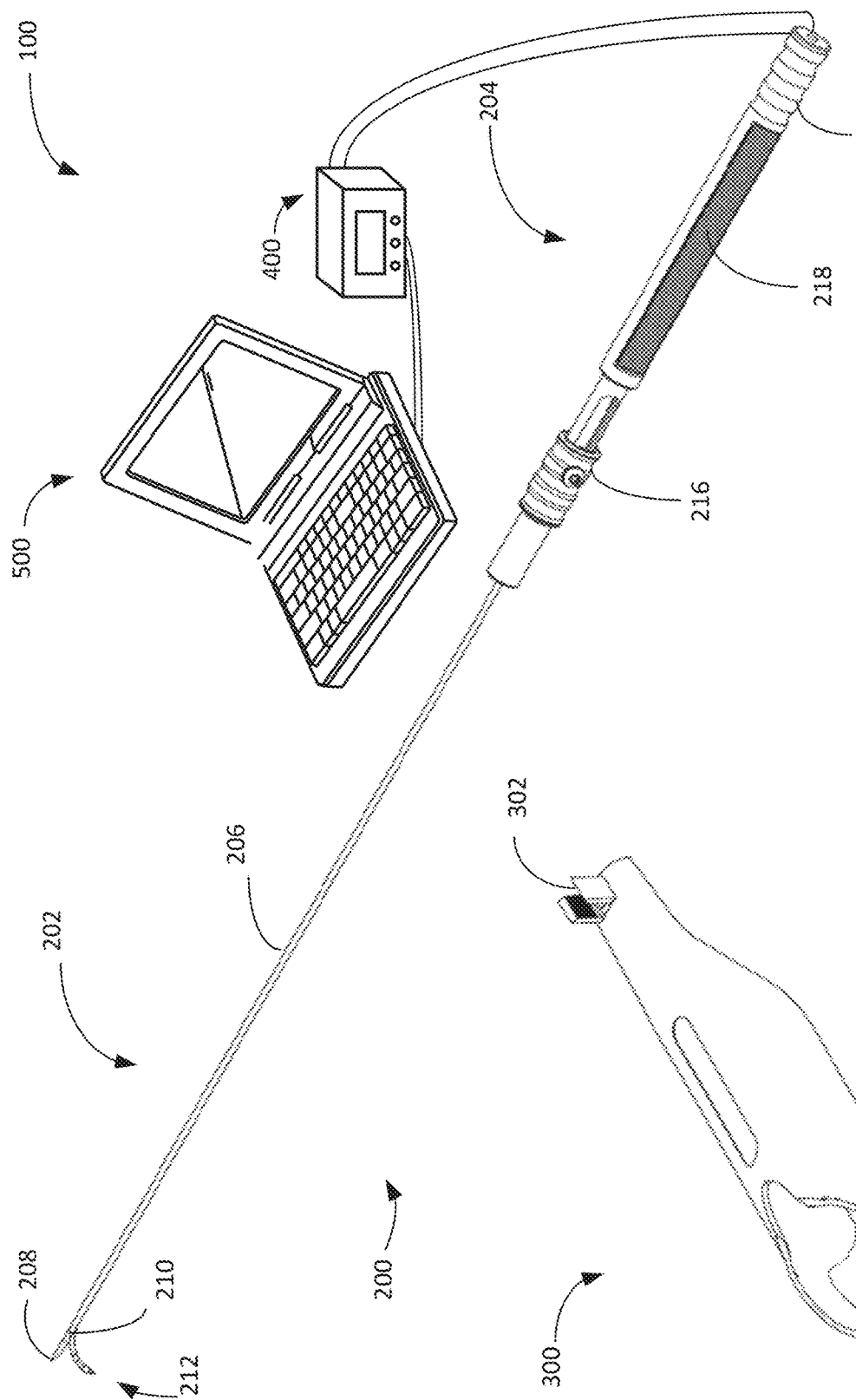
FIG. 1A illustrates an exemplary system for performing an ovarian procedure, constructed and operative in accordance with a non-limiting embodiment of the present invention.

The present invention is directed to systems and methods for performing a procedure on a body such as an ovary. As shown in FIG. 1A, system 100 for performing an ovarian procedure is now described. In FIG. 1A, components of the system are not depicted to scale on either a relative or absolute basis. Therapeutic needle assembly 200 includes distal region 202 and proximal region 204. Distal region 202 includes elongated shaft 206 with needle tip 208 at the distal end of elongated shaft 206 and port 210 proximal to needle tip 208. Needle tip 208 is constructed to pierce a vaginal wall and/or an ovarian wall. Therapeutic needle assembly 200 also includes therapeutic portion 212 slidably disposed within a lumen of elongated shaft 206. Therapeutic portion 212 may be deployed out of port 210, as shown in FIG. 1A, and is configured to emit energy therefrom (e.g., via one or more electrodes) after deployment.

Proximal region 204 of therapeutic needle assembly 200 preferably includes handle 214, actuator 216, and adapter interface 218. Actuator 216 is constructed to deploy therapeutic portion 212 out of port 210 when actuated. For example, actuator 216 may include a button depressable to unlock the actuator 216 and slide the actuator 216 distally to move therapeutic portion 212 distally such that therapeutic portion 212 is deflected out of side port 210 and curves as shown in FIG. 1A. Adapter interface 218 is constructed to secure therapeutic needle assembly 200 to an ultrasound probe via adapter 300. Adapter 300 is configured to be coupled to therapeutic needle assembly 200 and to an ultrasound probe. Advantageously, adapter 300 works with many commercially available ultrasound probes and permits therapeutic needle assembly 200 to be seamlessly used with a variety of probes. Adapter 300 preferably includes needle assembly interface 302 configured to be removably coupled to therapeutic needle assembly 200 (e.g., at adapter interface 218) and ultrasound probe interface 304 configured to be removably coupled to a vaginal ultrasound probe.

Additionally, system 100 includes generator 400 constructed to communicate with therapeutic portion 212. Generator 400 is configured to be electrically coupled to therapeutic needle assembly 200 to deliver energy to therapeutic portion 212 for emission into tissue. In addition, generator 400 may receive sensed information from one or more sensors of therapeutic needle assembly 200 to monitor operation of the assembly and the patient's anatomy during treatment. System 100 also preferably includes generator software 500, which may run on generator 400 or on a separate computer (as illustrated in FIG. 1A). Generator software 500 provides a user-friendly interface for a user (e.g., clinician, gynecologist, etc.) to monitor operation of therapeutic needle assembly 200 and the patient's anatomy during treatment.

Therapeutic needle assembly 200 and/or adapter 300 may be designed for treatment on a single patient and then are disposed of, while generator 400 and generator software 500 are reusable and interchangeable with multiple therapeutic needle assemblies and adapters.

Figure 1B:
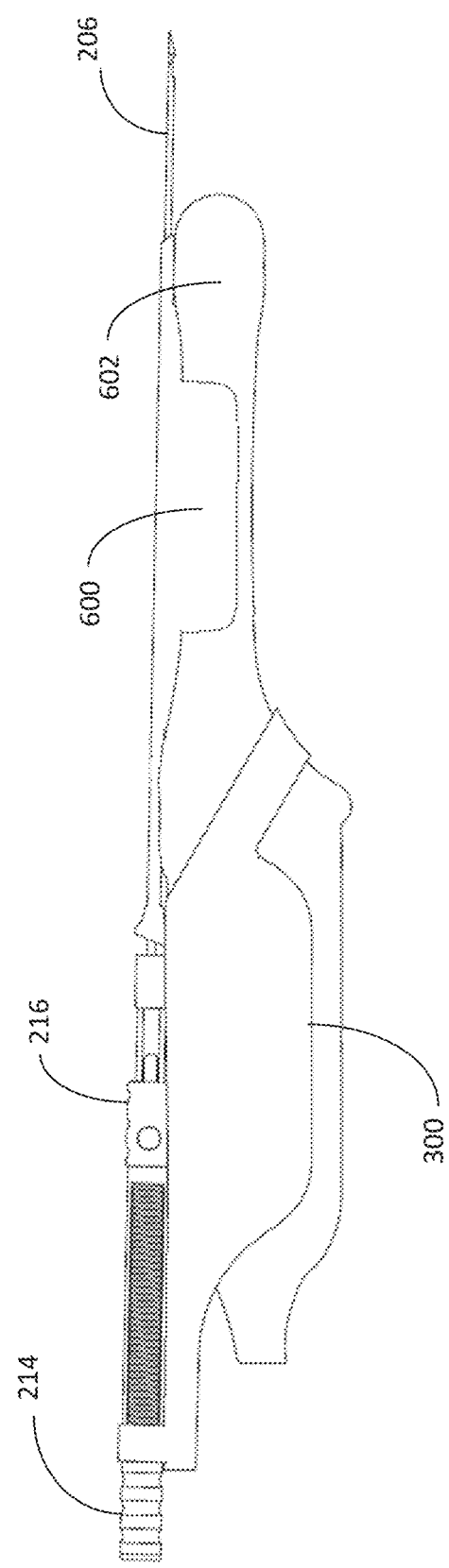
FIG. 1B illustrates an exemplary therapeutic needle assembly and adapter from the system of FIG. 1A assembled with an ultrasound probe and needle guide, in accordance with a non-limiting embodiment of the present invention.

FIG. 1B illustrates therapeutic needle assembly 200 and adapter 300 of system 100 coupled together and coupled to needle guide 600 and ultrasound probe 602. Needle guide 600 is configured to be coupled to ultrasound probe 602 and to receive elongated shaft 206 therethrough to stabilize the shaft during a procedure. Needle guide 600 may be a commercially available needle guide such as the Disposable Endocavity Needle Guide available from CIVCO Medical Solutions of Coralville, Iowa. Ultrasound probe 602 may be any commercially available ultrasound probe for vaginal use. For example, ultrasound probe 602 may be GE RIC5-9-D, GE RIC6-12-D, or RIC5-9W-RS ultrasound transducers available from GE Healthcare of Chicago, Ill. As will be readily understood by one skilled in the art, ultrasound probe 602 may be used with other ultrasound components, such as the display, used in combination with the probe. Needle guide 600 preferably assists to align therapeutic portion 212 to the ultrasound visualization plane or field of view formed from ultrasound probe 602 in a manner that ensures visability as it deploys, which may allow the operator to more precisely position and deliver the treatment in the desired location. As will be understood by a person having ordinary skill in the art, various elements may be combined into a single entity, such as the therapeutic needle assembly 200 and needle guide 600, needle assembly 600 and adapter 300, and the like.

Figures 2A, 2B:
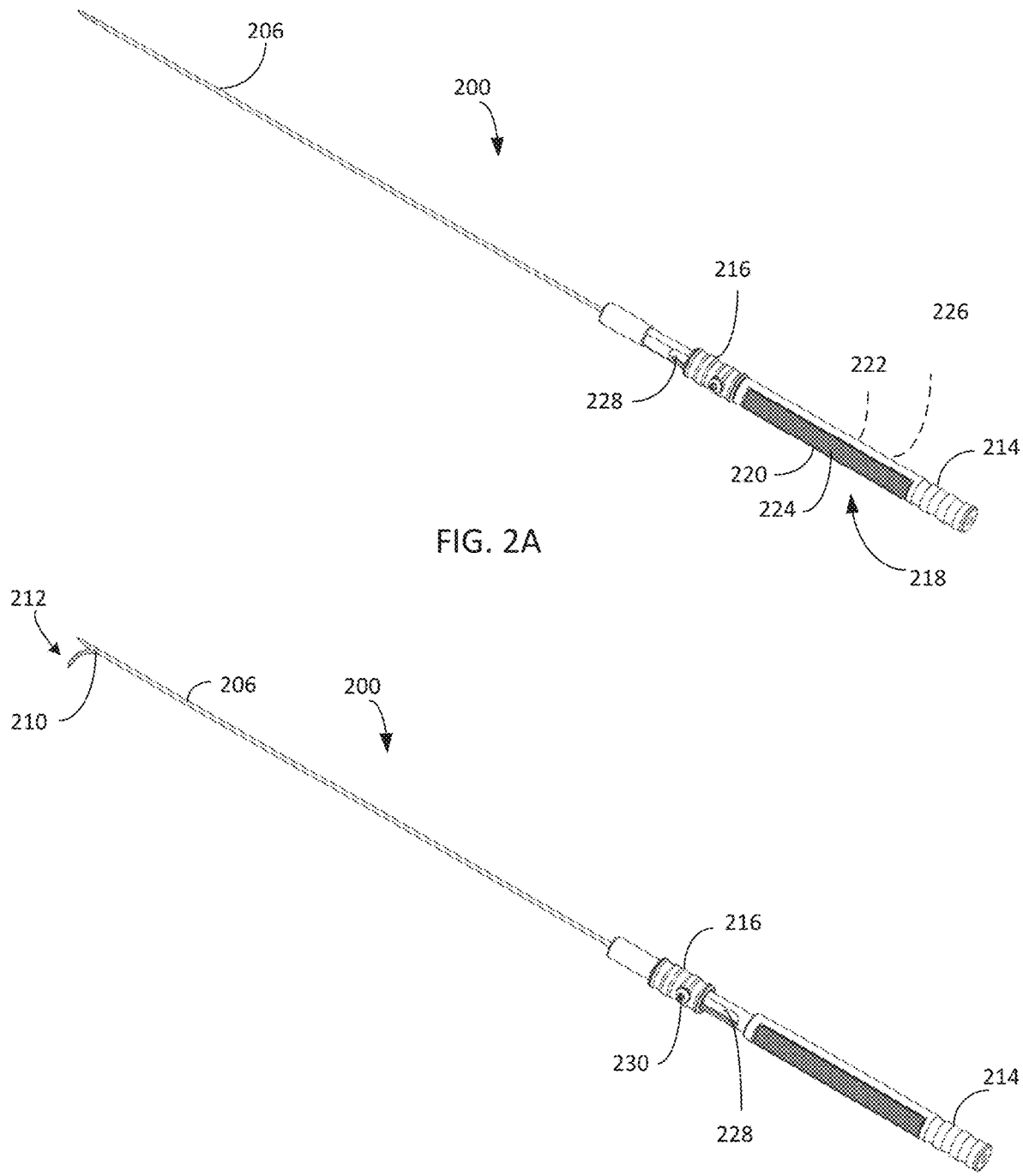
FIGS. 2A and 2B depict an exemplary therapeutic needle assembly from the system of FIG. 1A in a retracted state and a deployed state, respectively.

Referring now to FIGS. 2A and 2B, therapeutic needle assembly 200 is shown, respectively, in a retracted state and a deployed state. Handle 214 may include first notch 220 and second notch 222 on opposing surfaces to lock therapeutic needle assembly 200 to adapter 300 via needle assembly interface 302. First plurality of ribs 224 along first notch 220 and second plurality of ribs 226 along second notch 222 may be included to enhance locking. Channel 228 is disposed within handle 214 such that actuator 216 may move longitudinally to deploy and retract therapeutic portion 212 when trigger 230 (e.g., a button) is depressed. FIG. 2B illustrates the position after actuator 216 is actuated and therapeutic portion 212 is deployed out port 210.

Figure 2C:
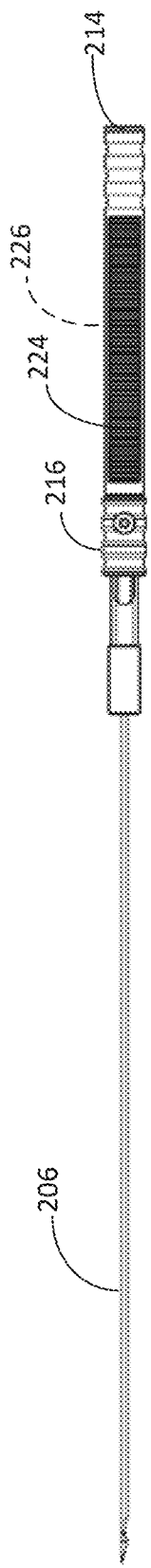
FIGS. 2C and 2D are side and top views of the exemplary therapeutic needle assembly in the retracted state.
Figure 2D:
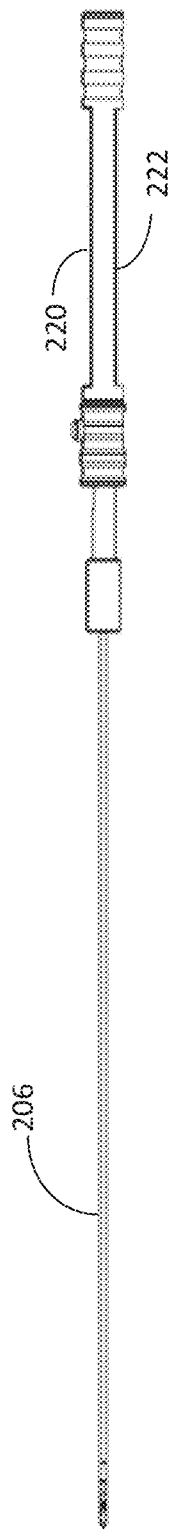
Figure 2E:
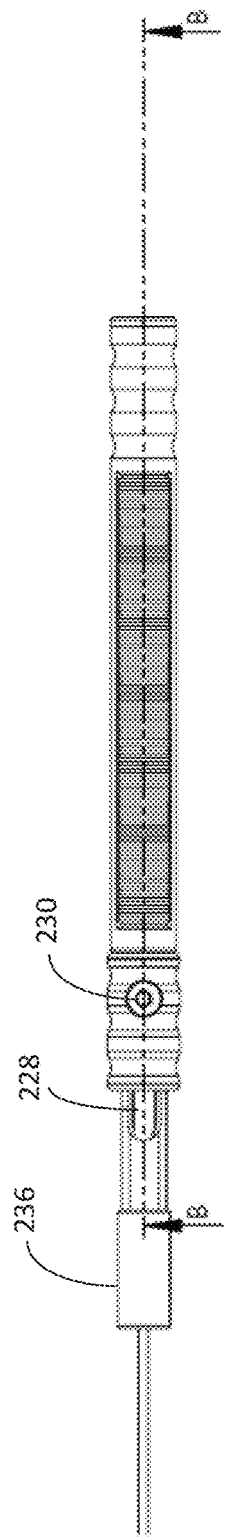
FIG. 2E shows a side view of the handle of the exemplary therapeutic needle assembly in the retracted, locked state over a cross-sectional view along the section line.
Figure 2F:
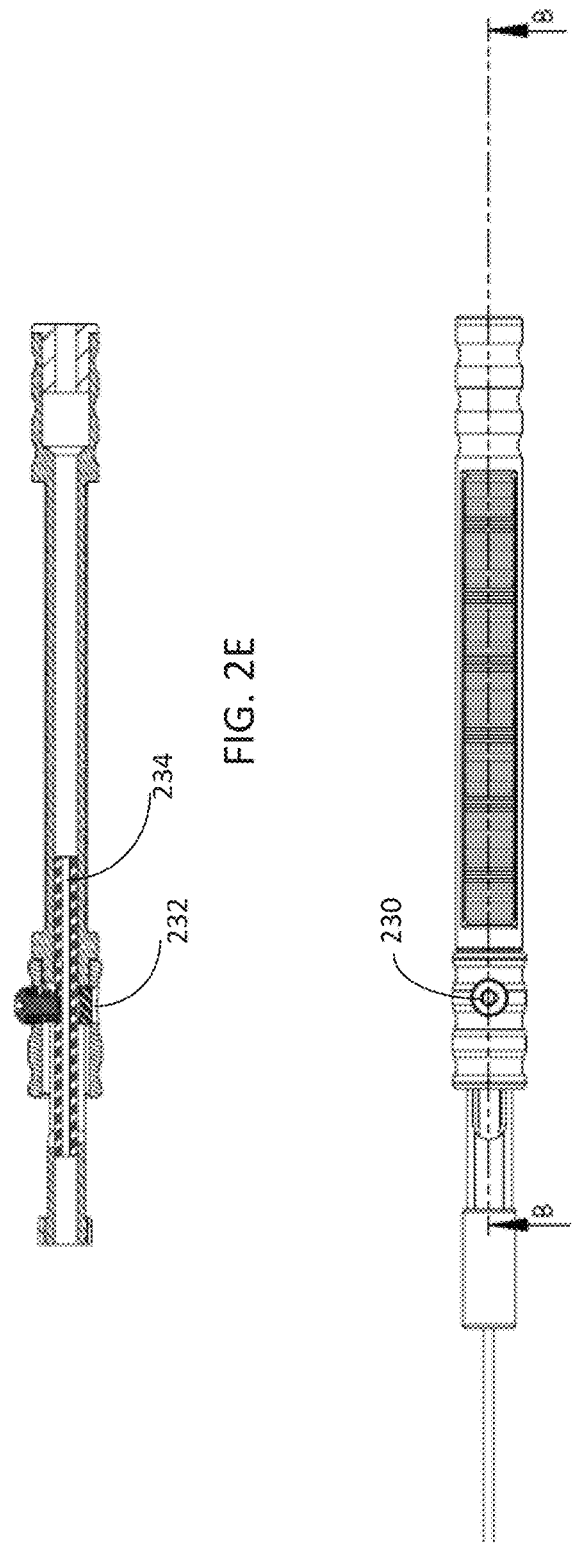
FIG. 2F shows a side view of the handle of the exemplary therapeutic needle assembly in the retracted, unlocked state over a cross-sectional view along the section line.
Figure 21:
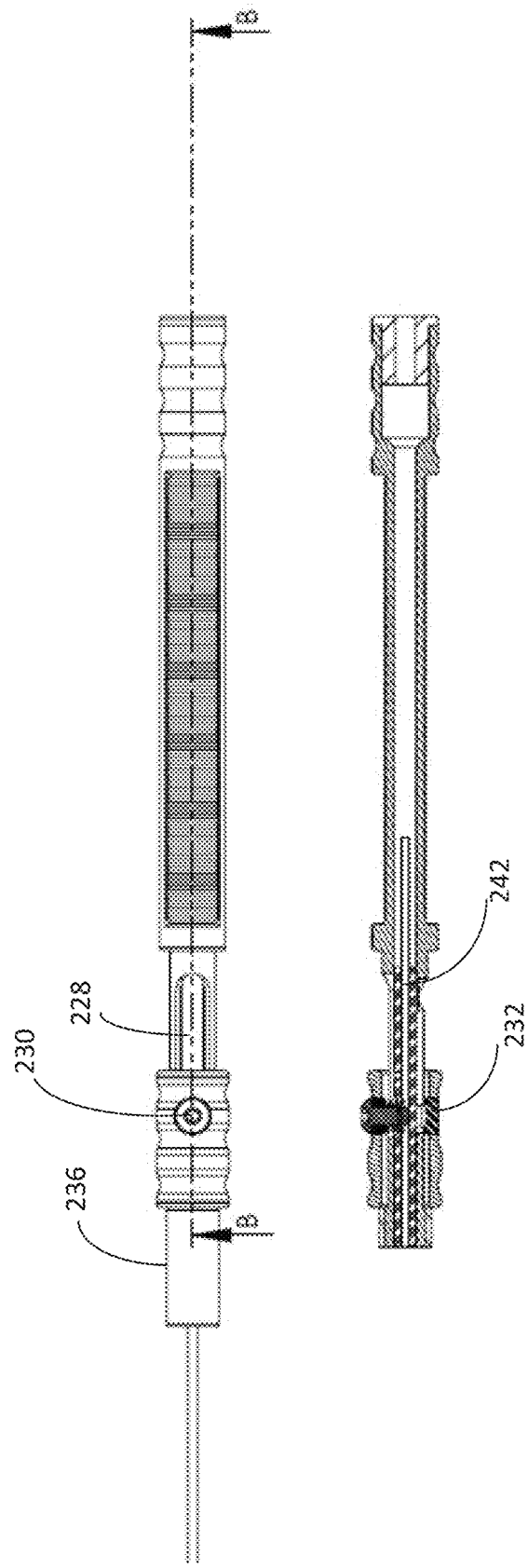

Reference is now made to FIGS. 2C-2I. Elongated shaft 206 extends from the distal end of handle 214. As explained above, adapter interface 218 on handle 214 may include first and second plurality of ribs 224, 226 at first and second notches 220, 222 to aid in the gripping and coupling to adapter 300. FIGS. 2C and 2D illustrate a side and top view of therapeutic needle assembly 200, respectively. Similarly, side and top views of therapeutic needle assembly 200 are shown in FIGS. 2G and 2H, with like components shown and along with a deployed therapeutic portion 212. FIGS. 2E, 2F, and 2I illustrate detailed and cross sectional views of handle 214: FIG. 2E illustrating a locked, retracted state, FIG. 2F illustrating an unlocked, retracted state, and FIG. 2I illustrates a deployed state. Handle 214 includes trigger 230 to control locking mechanism 232. When trigger 230 is depressed, locking mechanism 232 is released and actuator 214 can move advancement rail 234 along channel 228 for the purpose of deploying therapeutic portion 212 out port 210. Such deploying features may include a slider, knob, wheel, crank, or the like, which can be used to deploy/retract therapeutic portion 212. Stopper 236 is disposed on the distal end of handle 214 to prevent actuator 216 from moving past a desired distal point on handle 214. This may aid in limiting the distance therapeutic portion 212 may extend from port 210.

Figure 2J:
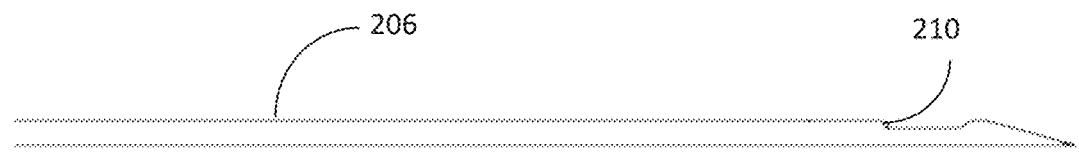
FIG. 2J is a side of the distal region of the exemplary therapeutic needle assembly.
Figure 2K:
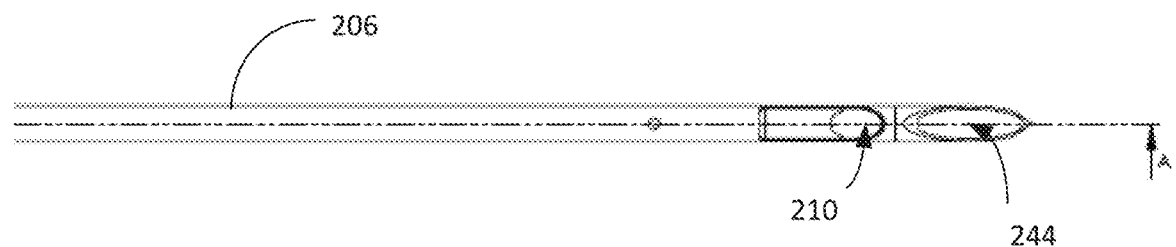
FIG. 2K shows the distal region rotated 90 degrees and shows inner components in the shaft, and FIG. JL shows the distal region, including inner components, flipped from the orientation in FIG. 2J.
Figure 2L:
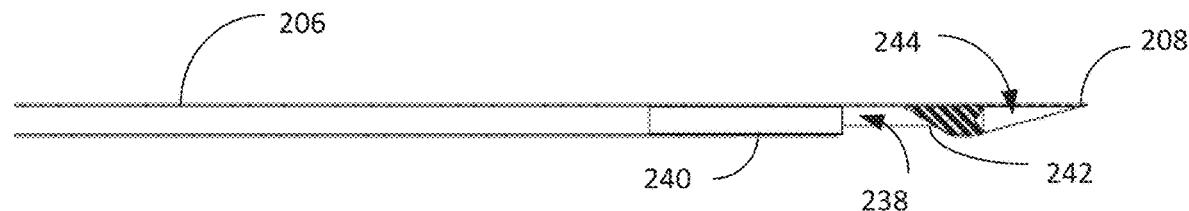
FIGS. 2G and 2H are side and top views of the exemplary therapeutic needle assembly in the deployed state.
FIG. 2I shows a side view of the handle of the exemplary therapeutic needle assembly in the deployed state over a cross-sectional view along the section line.
FIG. 2M is a cross-sectional view of the distal region of the exemplary therapeutic needle showing the therapeutic portion in the deployed state.

Reference is now made to FIGS. 2J-2L, which depict various views of elongated shaft 206. Elongated shaft 206 includes port 210 out of which therapeutic portion 212 may be deployed from lumen 238. Adjacent to port 210 is lubricant 240, e.g., a lubricious tube or coating, which is disposed within the lumen of elongated shaft 206 proximal to port 210. Lubricant 240, or a similar feature, is included to facilitate the transition of therapeutic portion 212 from a retracted state to a deployed state. It has been found that without such a lubricant feature, the therapeutic elements such as electrodes or sensors, or any component of therapeutic portion 212 may be damaged from the friction/contact to the edges of port 210 during deployment and/or retraction. Lubricant 240 may be a lubricious tube made from a biocompatible material that minimizes friction between the therapeutic portion 212 and elongated shaft 206, thus protecting its components. Examples of such a biocompatible material may be ultra-high-molecular-weight polyethylene or fluoropolymers.

Additionally or alternative, elongated shaft 206 may include a structure or configuration, such as a ramp or radiused curve, to facilitate transitioning of therapeutic portion 212 between the retracted state and the deployed state. Therapeutic portion 212 is additionally guided by angled interface 242, which forms the distal end of the lumen within elongated shaft 200 and also defines the distal end of port 210. Angled interface 242 guides therapeutic portion 212 to exit lumen 238 of elongated shaft 200 out port 210 at a desired angle to facilitate in positioning therapeutic portion 212 for treatment in its curved shape. Needle tip 208 also has needle cavity 244 formed therein. It has been found that forming needle cavity 244 by coring out an inner portion of needle tip 208 aids in piercing a vaginal wall and/or ovarian wall.

Figure 2M:
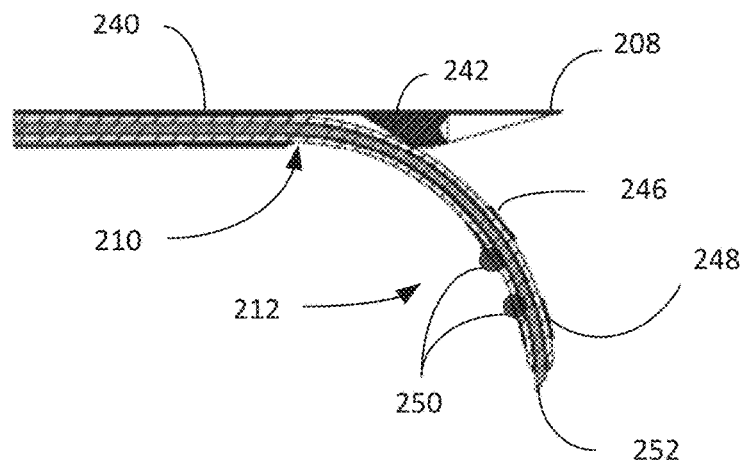

Referring now to FIG. 2M, a detailed view of therapeutic portion 212 deployed out of port 210 is provided. Therapeutic portion 212 preferably forms a curved shaped when deployed, as illustrated. Therapeutic portion 212 is configured to deliver energy after deployment and may include one or more electrodes—illustratively, first electrode 246 and second electrode 248. First electrode 246 and/or second electrode 248 may deliver energy, e.g., radiofrequency energy, to effect treatment. First and second electrodes 246, 248 may be comprised of metallic bands, coils, wires (e.g., wound or braided), laser cut tubing, or slotted tubular structures. The shaft of therapeutic portion 212 may have a pre-set shape that may serve multiple purposes such as anchoring the device within an ovary (to limit the risk of the device moving due to patient movement or user error), orienting therapeutic portion 212 to be more normal to the ultrasound probe in order to increase echogenicity, and increasing the total length of therapeutic portion 212 that can be located within the ovary. The pre-set shape may also enable therapeutic portion 212 to more readily reach different locations within the ovary, as compared to a straighter element, and thereby reduce the amount of manipulation by therapeutic needle assembly 200 and/or reduce the number of punctures to the ovary. Additionally, the elongated shaft 206, therapeutic portion 212, and/or needle tip 208 may contain echogenic material and/or gas to enhance echogenicity.

Additionally, therapeutic needle assembly 200 (e.g., at therapeutic portion 212) may include one or more sensors to detect parameters such as temperature, impedance, or other parameters that could guide therapy delivery. For example, sensors 250 may be located on the inner surfaces of first and second electrodes 246, 248, as illustrated. In one example, sensors 250 are thermistors used to measure temperature. Generator 400 (not shown) may use detected parameters sensed by the sensor(s) along with generator software 500 (described in FIGS. 7-9) to monitor operation of therapeutic needle assembly 200 and/or the patient during treatment. For example, a treatment could be automatically stopped when certain temperature, time, power, and/or impedance thresholds have been crossed. The impedance values could also be used to determine the relative location of therapeutic portion 212 within an ovary. Conductive needle 252 may form the distal tip of therapeutic portion 212 to sense electrical activity for communication with generator 400 to determine one or more parameters such as impedance. Advantageously, conductive needle 252 has a sharp tip to facilitate movement through tissue during therapeutic portion 212 deployment.

Figure 3A:
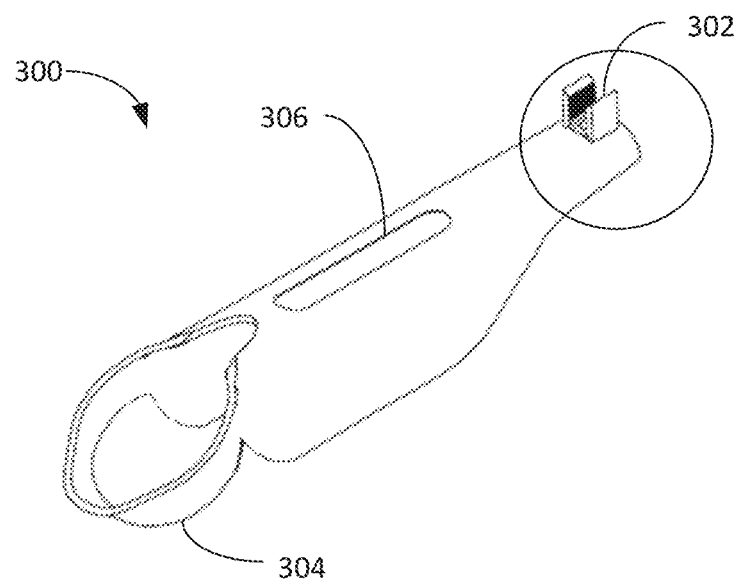
FIG. 3A illustrates an exemplary adapter from the system of FIG. 1A
Figure 3B:
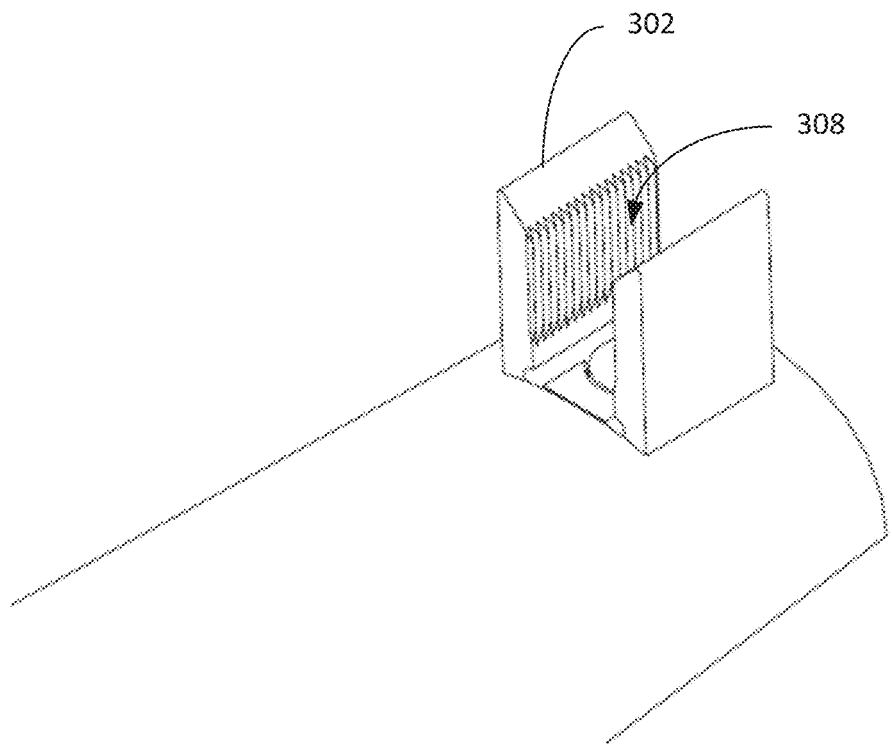
FIG. 3B illustrates a close-up version of an exemplary therapeutic needle interface of the adapter.

Referring now to FIGS. 3A and 3B, adapter 300 of system 100 preferably includes needle assembly interface 302, ultrasound probe interface 304, and actuator track 306. Adapter 300 may be saddle shaped and include ultrasound probe interface 304 to secure adapter 300 to an ultrasound probe. Ultrasound probe interface 304 may be collar shaped and looped around a portion of the ultrasound probe between a proximal end and a distal end of the ultrasound probe. The sides of adapter 300 may be placed around a more proximal region of an ultrasound probe. Adapter 300 can be snapped, strapped, clamped, or any similar means in order to be adaptable to a variety of ultrasound probes. As shown in FIGS. 3A and 3B, needle assembly interface 302 on the proximal region of adapter 300 includes needle assembly interface ribs 308 for gripping therapeutic needle assembly 200 when inserted. Needle assembly interface 302 is constructed to couple with adapter interface 218 of therapeutic needle assembly 200 such that therapeutic needle assembly 200 may be attached longitudinally to the ultrasound probe and may be removed, rotated, and reattached when desired during treatment. The limited rotation that results can be useful in maintaining therapeutic portion 212 within the ultrasound visualization plane or field of view. When therapeutic needle assembly 200 is inserted, actuator track 306 facilitates a smoother movement for actuator 216.

In accordance with another aspect of the present invention, needle assembly interface 302 and needle assembly 200 may be configured to allow a variable amount of rotation or a specific rotation, e.g., up to 90 degrees or up to 180 degrees, without having to decouple the needle assembly interface from the adapter interface. For example, as shown in FIG. 3C, therapeutic needle assembly 200 may be rotated while needle assembly interface 302 remains engaged with adapter interface 218 via handle 214 to reorient port 210 within field of view FOV of the ultrasound probe. Accordingly, at any given orientation of therapeutic needle assembly 200, therapeutic portion 212 will protrude from port 210 within the ovary within the field of view of the ultrasound probe. FOV is limited by the ultrasound probe, and thus, as will be understood by a person having ordinary skill in the art, rotation of therapeutic needle assembly 200 may be limited such that therapeutic portion 212 will always protrude from port 210 within the field of view of the ultrasound probe. For example, therapeutic needle assembly 200 may be rotated up to 180 degrees from a first orientation to a second orientation. In some embodiments, as shown in FIG. 3C. therapeutic needle assembly 200 may only be rotated up to 90 degrees from a first orientation to a second orientation, so long as therapeutic portion 212 remains within the field of view of the ultrasound transducer during operation.

In accordance with another aspect of the present invention, adapter interface 218 and needle assembly interface 302 may permit reorientation of therapeutic needle assembly 200 relative to adapter 300 between more orientations than a first orientation and a second orientation, for example, a third orientation or a fourth orientation. Additionally, adapter interface 218 and needle assembly interface 302 may lock together at any orientation. At any orientation, therapeutic needle assembly 200 may be locked in position.

Figure 4:
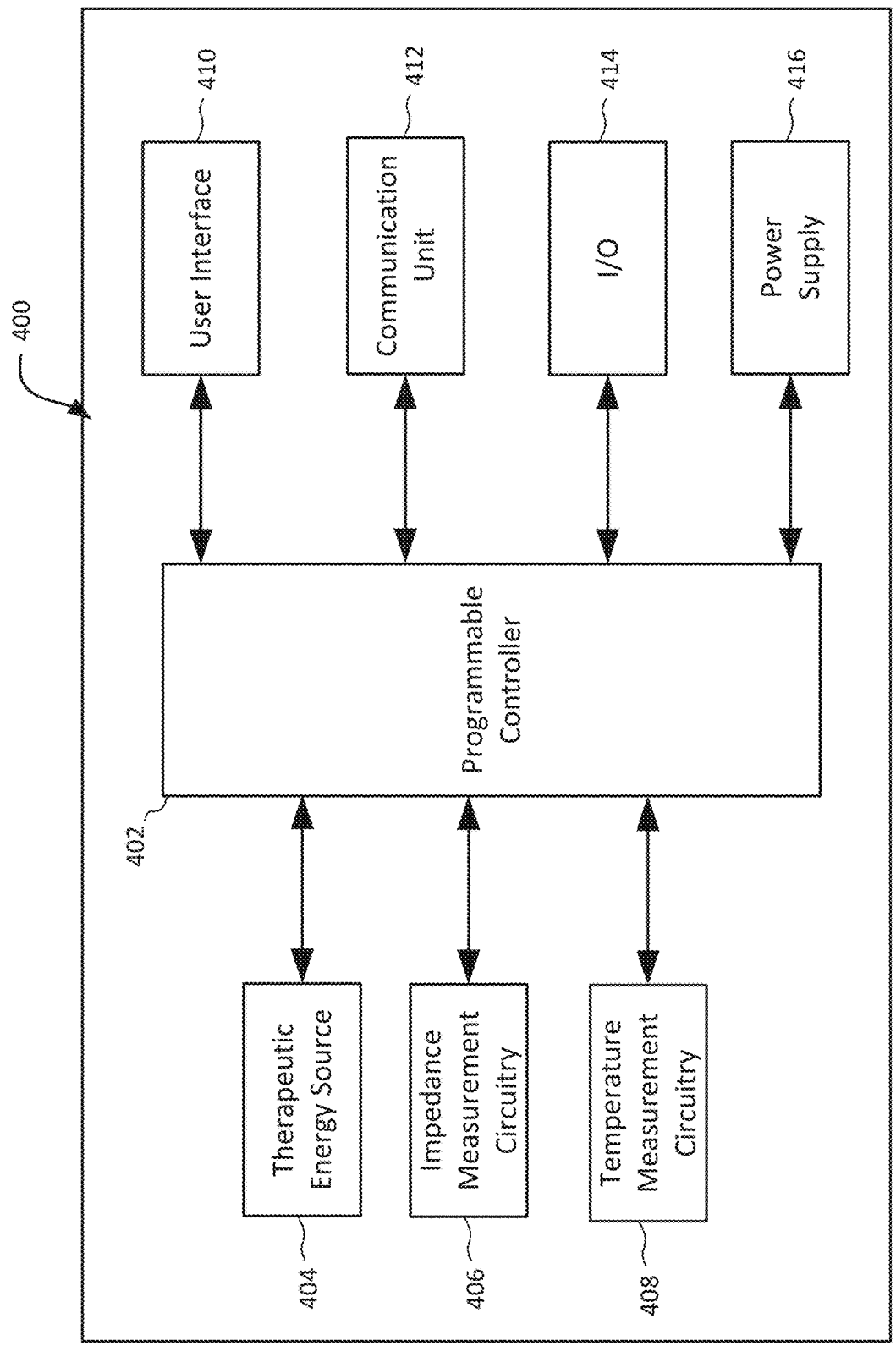
FIG. 4 shows a schematic diagram of an exemplary generator of the system of FIG. 1A.

Referring to FIG. 4, a generalized schematic diagram of the internal functional components of generator 400 is now described. Generator 400 may include programmable controller 402 operatively coupled to therapeutic energy source 404, impedance measurement circuitry 406, temperature measurement circuitry 408, graphical user interface 410, communications unit 412, input and output circuitry (I/O) 414, and/or power supply 416.

Programmable controller 402, is electrically coupled to, and designed to control, the internal functional components of generator 400. Controller 402 may comprise one or more commercially available microcontroller units that may include a programmable microprocessor, volatile memory, nonvolatile memory such as EEPROM for storing programming, and nonvolatile storage, e.g., Flash memory, for storing firmware and a log of system 100 operational parameters and patient data. The memory of controller 402 stores program instructions that, when executed by the processor of controller 402, cause the processor and the functional components of generator 400 to provide the functionality ascribed to them herein. Controller 402 is designed to be programmable such that programming data is stored in the memory of controller 402 and may be adjusted using generator software 500. For example, the memory of controller 402 may store program instructions that, when executed by the processor of controller 402, cause the processor to receive and store information indicative of, e.g., the patient's ovarian volume(s). For example, using ultrasound technology known in the art, a clinician may receive a patient's ovarian volume based on measurements such as the length, width, and/or depth, of an ovary. Specifically, the clinician may use a program that measures the length, width, and/or depth of an ovary, e.g., by clicking different spatial points on a graphical user interface displaying an ultrasound of the patient's ovary, and calculates the ovarian volume based on the measurements.

The clinician may then provide the ovarian volume as user input to controller 402, such that the processor may store and generate information based on the ovarian volume input. For example, the memory of controller 402 may store program instructions that, when executed by the processor of controller 402, cause the processor to, based on the ovarian volume and desired outcome, generate recommended/required ablation parameters, recommended/required number of ablations, recommended/required volume of ovarian ablation. Thus, for a given patient, the clinician can know the volume of ovarian ablation needed per ovary, and how many ablations and at what parameters to deliver the ablation to the patient to ablate the volume of ovarian ablation needed.

Further, the processor may execute instructions to cause the graphical user interface to display the generated recommended/required ablation parameters, recommended/required number of ablations, and/or recommended/required volume of ovarian ablation, in addition to set ablation parameters, power settings, number of completed ablations, number of remaining ablations, percentage of ovarian volume ablated, and/or percentage of ovarian volume remaining to be ablated. Information related to the recommended or set ablation parameters may be in the form of a table, e.g., a lookup table, stored in the memory, and displayed to the clinician via the graphical user interface.

Moreover, the processor may automatically recalculate any of the above information after each ablation performed by the clinician, and display the recalculated information after each ablation such that the clinician will know the remaining volume of ovarian ablation needed per ovary, and how many ablations and at what parameters to deliver the ablation to the patient to ablate the remaining volume of ovarian ablation needed. Thus, for a given ovarian volume of a patient, the processor knows how much volume of ovarian tissue will be ablated for any given set of parameters, and accordingly, how much percentage of ovarian tissue remains to be ablated to achieve the desired ablation therapy, e.g., 5%, 7.5%, 10%, 12%, or 15% of the ovary ablated. For example, for a given patient's ovarian volume, the processor may determine that five ablations are needed to ablate 5-10% of the ovary, and the processor communicates what volume of ovarian tissue will be ablated per ablation for a given set of ablation parameters, e.g., power level, or time and temperature, to the clinician. This information may be retrieved by the clinician via a table, e.g., a lookup table. Accordingly, after one ablation has been performed by the clinician on the patient's ovary, the processor will adjust the data and display that four remaining ablations are needed. In addition, if the clinician did not complete the first ablation, e.g., cut it off short, or performed the ablation at parameters other than recommended/required by the processor, the processor will readjust and display an adjusted amount of ablations remaining to achieved the desired ablation therapy, to account for the clinician's deviation from the recommended/required settings.

As will be readily understood to one skilled in the art, while FIG. 4 is illustrated to show one programmable controller, multiple programmable controllers may be utilized.

Therapeutic energy source 404 is designed to provide energy (e.g., RF energy) from generator 400 to therapeutic portion 212 to deliver energy to first and second electrodes 246, 248 and treat the ovarian tissue. Energy may be applied in a continuous or pulsed fashion. Impedance measurement circuitry 406 and temperature measurement circuitry 408 are designed to sense one or more parameters of sensors 250 and/or conductive needle 252 such as impedance or temperature. System sensors 250 and/or conductive needle 252 may generate one or more signals indicative of the sensed parameter(s) for processing and/or transmission to generator software 500. Such parameters may be used to assist in treatment or to confirm proper functioning of system 100.

Graphical user interface 410 is designed to receive user input and, optionally, to display information to the user. Graphical user interface 410 may include buttons for receiving user input and a display for displaying information to the clinician (see FIGS. 10-13). As will be readily apparent to one skilled in the art, graphical user interface 410 is not limited thereto and may use one or more of a trigger, a plunger, a touch screen, a keypad, a microphone, a speaker, a trackball, or the like.

Communication unit 412 is designed to transmit information, such as signals indicative of sensed parameters and the like, to a remote location such as a computer running generator software 500. Communication unit 412 may include circuitry; e.g., WiFi, Bluetooth, and/or cellular chipsets; configured for wireless communication over a network such as the Internet, a local network, or a telephone network using techniques known in the art.

Input and output circuitry (I/O) 414 may include ports for data communication such as wired communication with a computer and/or ports for receiving removable memory, e.g., SD card, upon which program instructions or data related to generator 400 use may be stored. In one embodiment, I/O 414 comprises ports, and corresponding circuitry, for accepting cables such that generator 400 is electrically coupled to a computer running generator software 500.

Power supply 416 powers the electrical components of generator 400 and may comprise a primary cell or battery, a secondary (rechargeable) cell or battery or a combination of both. Alternatively, power supply 416 may be a port to allow generator 400 to be plugged into a conventional wall socket for powering components and/or recharging one or more batteries of generator 400. In one embodiment, power supply 416 comprises one or more ports and one or more cables that enable generator to be powered from the computer, e.g., via cables, running generator software 500.

Figure 5:
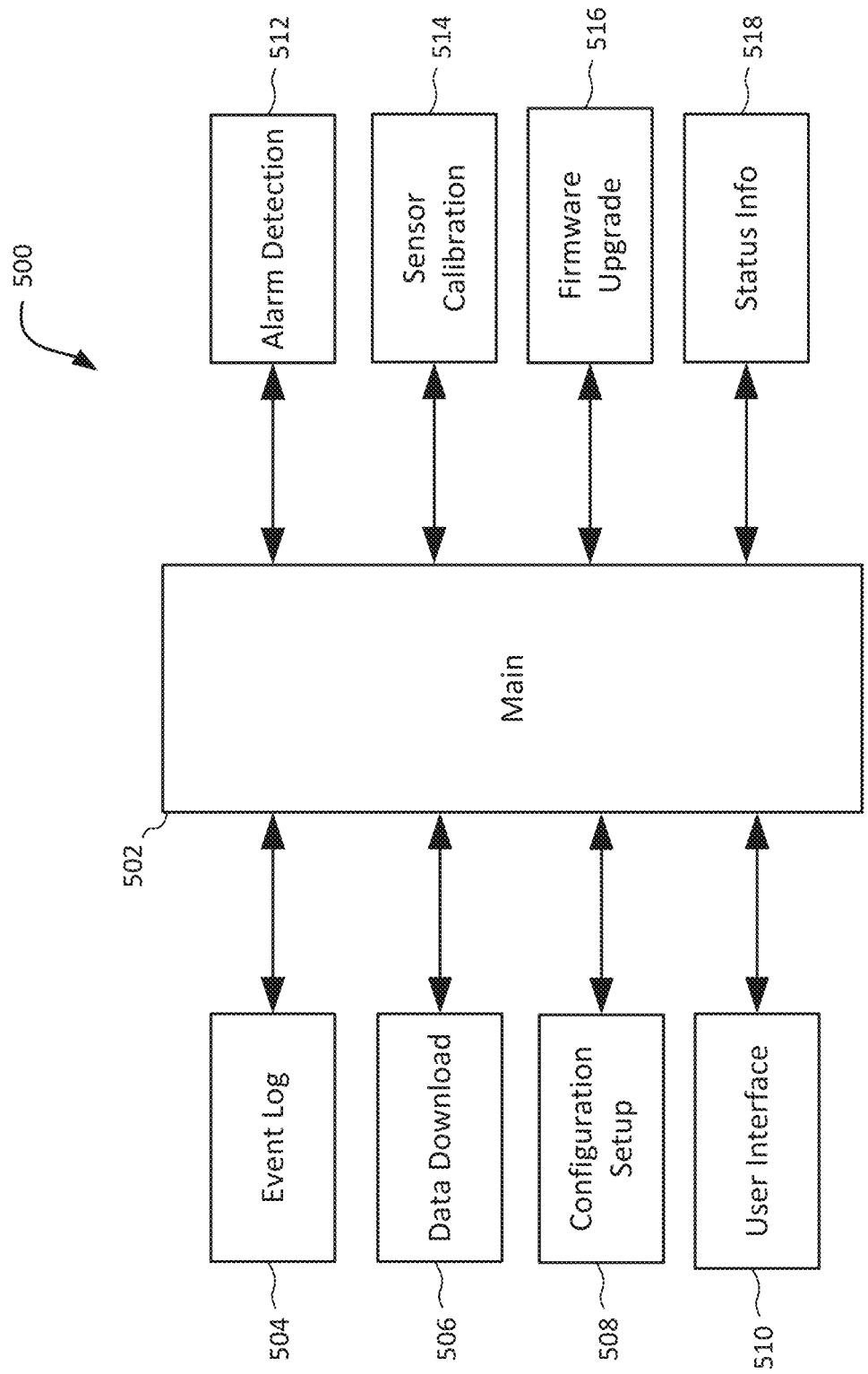
FIG. 5 shows a schematic diagram of the functional components of exemplary generator software of the system of FIG. 1A.

Referring now to FIG. 5, generator software 500 is now described. Generator software 500 comprises a number of functional blocks, schematically depicted in FIG. 5, including main block 502, event logging block 504, data download block 506, configuration setup block 508, user interface block 510, alarm detection block 512, sensor calibration block 514, firmware upgrade block 516, and status information block 518. The software preferably is written in C++ and employs an object oriented format. In one preferred embodiment, the software is configured to run on top of a Microsoft Windows™ (a registered trademark of Microsoft Corporation, Redmond, Wash.), Mac, or Unix-based operating system, such as are conventionally employed on desktop and laptop computers. The computer running generator software 500 preferably includes a data port, e.g., USB port or comparable wireless connection, that permits generator 400, an external monitoring component, and/or a mobile device running mobile application to be coupled thereto. Alternatively, or additionally, the computer may include wireless circuitry; e.g., conforming to the IEEE 802.11 standards, the 3G, 4G, 5G, LTE, or other cellular standards, and/or Bluetooth standards; thereby enabling generator 400, an external monitoring component, and/or a mobile device running mobile application to communicate wirelessly with the computer running generator software 500.

As will be readily apparent to one skilled in the art generator software 500 may run on a separate computer (as illustrated in FIG. 1A) such as a conventional laptop, desktop, tablet, smartphone, and the like, or may run on generator 400.

Main block 502 preferably includes a main software routine that executes on the clinician's computer, and controls overall operation of the other functional blocks. Main block 502 enables the clinician to download event data and alarm information stored on generator 400 to his office computer, and also permits generator software 500 to receive signals indicative of sensed parameters from generator 400. Main block 502 further is configured to execute routines to calculate parameters based on sensed parameters and/or store information related to treatments. For example, main block 502 is configured to execute a routine to measure impedance and/or temperature using signals indicative of impedance or temperature sensed at therapeutic portion 212. As another example, main block 502 is configured to execute a routine to store (and cause display) of the number of ablations per ovary and/or per patient and/or other information and parameters as previously described. Main block 502 further is configured to execute routines to calculate data for display based on input received at User Interface block 510. Main block 502 also enables the clinician to upload firmware updates and configuration data to generator 400.

Event log block 504 is a record of operational data downloaded from generator 400, and may include, for example, measurement times, real-time sensed parameters, parameters previously sensed, sensor data, battery current, battery voltage, battery status, number of ablations per ovary and/or per patient, and the like. The event log also may include the occurrence of events such as alarms or other abnormal conditions. Event log block 504 may further include a record of data inputted at user interface block 510 such as treatment termination.

Data download block 506 is a routine that commands generator 400 to transfer data to generator software 500 for download after generator 400 is coupled to the computer running generator software 500. Data download block 506 may initiate, either automatically or at the instigation of the clinician via user interface block 510, downloading of data stored in the event log.

Configuration setup block 508 is a routine that configures the parameters stored within generator 400 that control operation of the respective component/application. The parameters may determine, if past a predetermined threshold, to alert the user. Such interval timing parameters may be reconfigured by block 508. Interval timing settings transmitted to generator 400 from generator software 500 also may determine when and how often event data is written to the memory in the respective component/application.

User interface block 510 handles receipt of user input, e.g., ovarian volume, at the computer running generator software 500 and display of information retrieved from generator 400, and data download block 506, and presents that information in an intuitive, easily understood format for clinician review such as numbers, wave forms, text, a plot, a chart, a graph, or the like. Such information may include status of generator 400, measurement times, real-time sensed parameters, parameters previously sensed, parameters calculated using sensed parameters, sensor data, battery current, battery voltage, battery status, and the like.

Alarm detection block 512 may include a routine for evaluating the data retrieved from generator 400 and flagging abnormal conditions for the clinician's attention. For example, alarm detection block 512 may flag when a parameter sensed by system sensors 250, is above a first predetermined threshold or below a second predetermined threshold, as further explained in FIGS. 7-12.

Sensor calibration block 514 may include a routine for testing or measuring drift, of system sensors 250. Block 514 may then compute offset values for correcting measured data from sensors 250, and transmit that information to generator 400 for storage in the nonvolatile memory of controller 402.

Firmware upgrade block 516 may comprise a routine for checking the version numbers of the controller firmware installed on generator 400, and identify whether upgraded firmware exists. If so, the routine may notify the clinician and permit the clinician to download revised firmware to generator 400, in nonvolatile memory.

Status information block 518 comprises a routine for interrogating generator 400 to retrieve current status data from generator 400. Such information may include, for example, battery status, version control information for the firmware and hardware currently in use, and sensor data.

In addition, generator software 500 may further include a functional block for determining whether an appropriate needle assembly is coupled to the generator. For example, when a needle assembly is disposable, generator software 500 will ensure that the same needle assembly is not being used more than once. Accordingly, the needle assembly may include, e.g., a chip or an identification tab such as an RFID or barcode, that stores information regarding the needle assembly including whether it has been previously used. Upon reading of the chip or identification tab of the needle assembly by the generator, generator software 500 may permit subsequent ablation if it determines that the needle assembly is appropriate, or prevent subsequent ablation if it determines that the needle assembly is inappropriate.

Figure 6A:
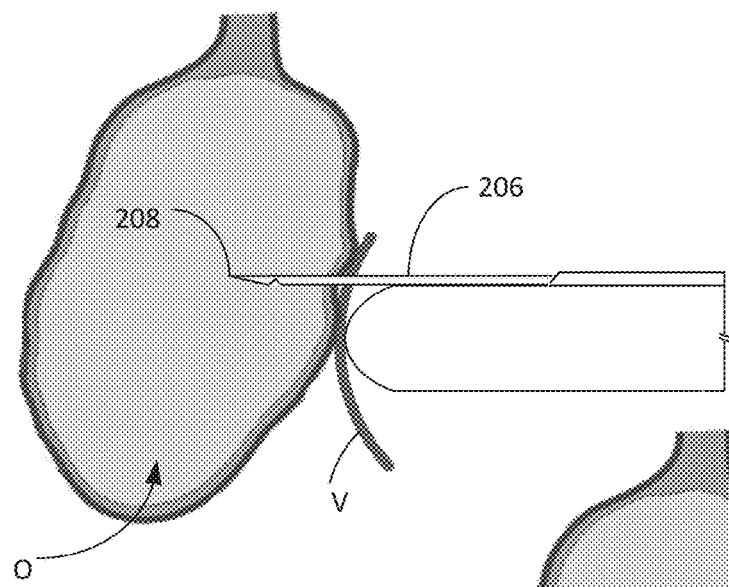
FIGS. 6A-6I illustrate an exemplary method for performing an ovarian procedure, in accordance with a non-limiting embodiment of the present invention.
Figure 6B:
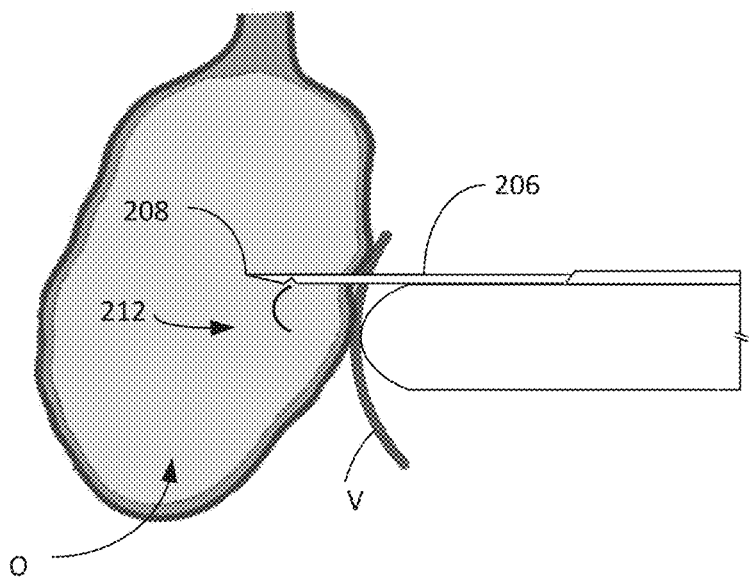

Reference is now made to FIGS. 6A-6F, which depict an example of a method for treating ovarian tissue utilizing therapeutic needle assembly 200, as described herein. In this example, therapeutic needle assembly 200 has been coupled to a vaginal ultrasound probe via adapter 300 and needle guide 600 is used. The operator positions elongated shaft 206 having therapeutic portion 212 disposed therein in a retracted state under ultrasound guidance using the ultrasound probe into the vagina. Needle tip 208 of elongated shaft 206 pierces the vaginal wall V and the ovarian wall. FIG. 6A illustrates accessing a target region proximate to ovarian tissue within the patient after advancing needle tip 208 through vaginal wall V, through the ovarian wall, and into ovary O. Once elongated shaft 206 is positioned in a first orientation, FIG. 6B illustrates deploying therapeutic portion 212. The operator then delivers energy to the treatment zone via generator 400 and therapeutic portion 212, for example, utilizing parameters described in U.S. Patent Publication Nos. 2016/0220302, 2017/0215949, and 2018/0110554 to Zairns, the entire contents of each of which are incorporated herein by reference. Energy may be delivered to heat (e.g., ablate) tissue in the treatment zone at a level and for a duration sufficient to effect treatment. For example, energy may be applied in the ovary over the course of multiple ablations to treat polycystic ovary syndrome (PCOS).

Figure 6C:
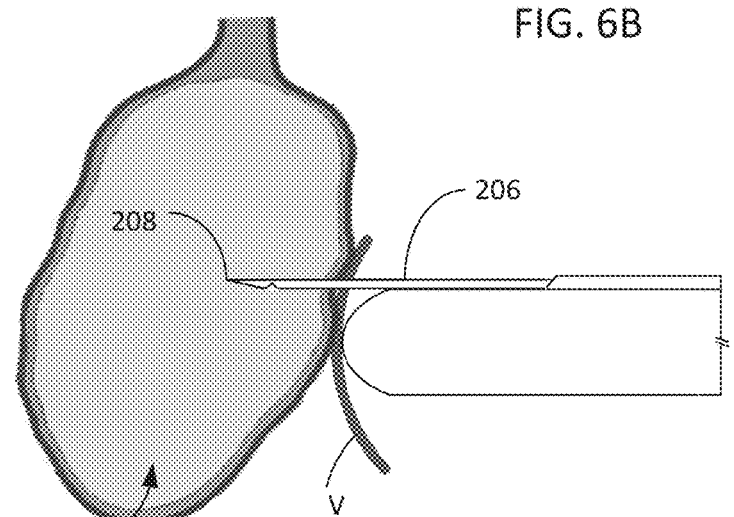

After energy delivery is complete, therapeutic portion 212 is retracted into elongated shaft 206, as shown in FIG. 6C. Without removing elongated shaft 206 from ovary O, the operator may rotate therapeutic needle assembly 200 with respect to adapter 300 or may decouple therapeutic needle assembly 200 from adapter 300 (e.g., by detaching the adapter interface from the therapeutic needle interface), flip/rotate therapeutic needle assembly 200 a predetermined amount (e.g., within a rotation range spanning up to 180 degrees), and reattach the adapter interface to adapter 300 if the adapter interface was detached from the therapeutic needle interface. This flipping may occur while the distal region remains in place (other than the rotation) in ovary O.

For example, as shown in FIG. 6B, therapeutic needle assembly 200 initially may be introduced into ovary O along the x-axis, such that port 210 of therapeutic needle assembly 200 points downward toward the y-axis. Accordingly, therapeutic portion 212 will be deployed along the y-axis in a plane formed by the x-axis and the y-axis. Upon retraction of therapeutic portion 212 into elongated shaft as shown in FIG. 6C, therapeutic needle assembly 200 may be rotated up to 90 degrees in either direction about the x-axis. For example, rotating therapeutic needle assembly 200 90 degrees in a clockwise direction about the x-axis from the position illustrated in FIG. 6C will cause port 210 to point out of the page toward the z-axis, and rotating therapeutic needle assembly 200 90 degrees in a counter-clockwise direction from the initial position illustrated in FIG. 6C about the x-axis will cause port 210 to point into the page toward the z-axis. Accordingly, therapeutic needle assembly 200 may be rotated any amount within an overall range of 180 degrees, which may be limited by the field of view of the ultrasound probe. For example, referring back to FIG. 3C, therapeutic needle assembly 200 may be rotated up to 45 degrees in either direction about the x-axis, providing an overall range of rotation within 90 degrees, such that port 210 and accordingly therapeutic portion 212 remain within the field of view FOV of the ultrasound probe. As will be understood by a person having ordinary skill in the art, therapeutic needle assembly 200 may be rotated to any orientation within the overall range of 180 degrees while the ultrasound probe remains in place, and locked in the desired position.

Figure 6D:
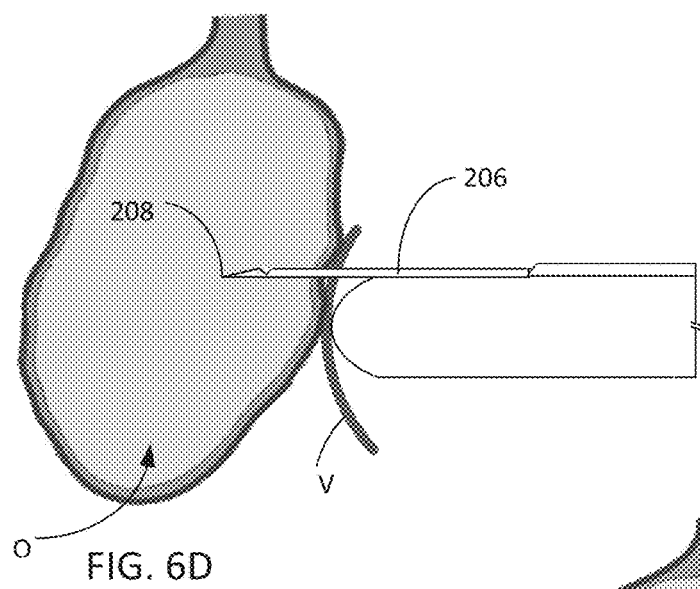
Figure 6E:
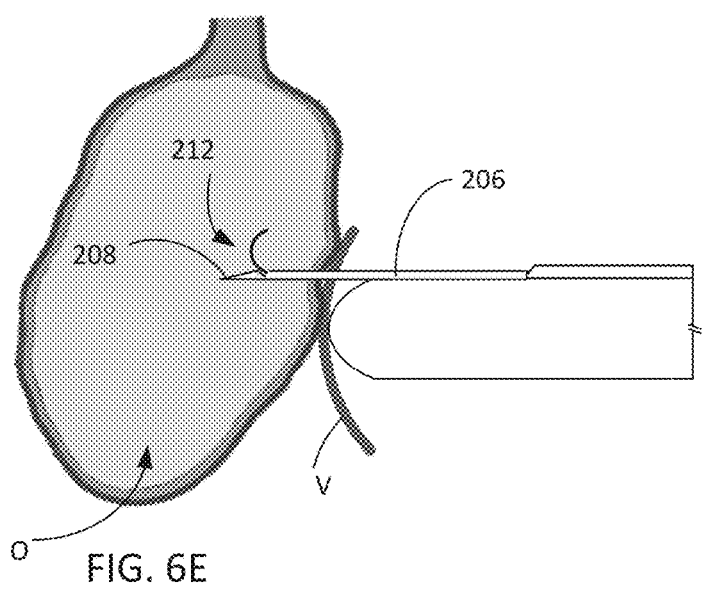
Figure 6F:
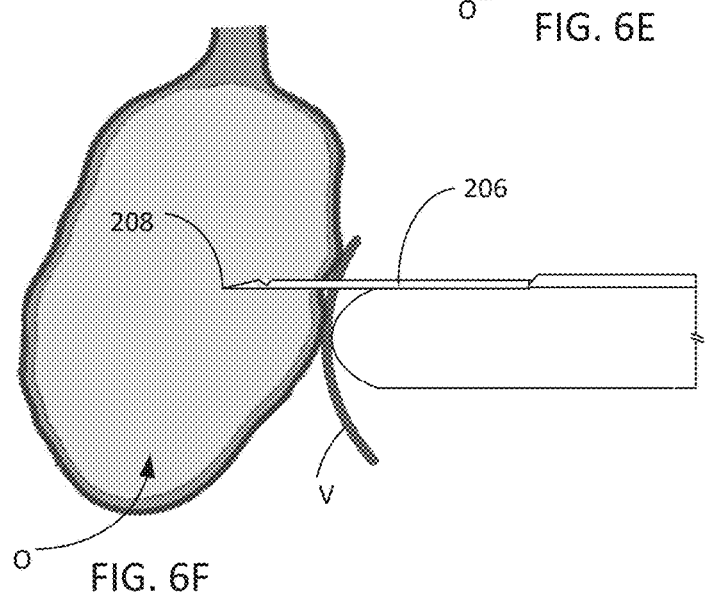
Figure 6G:
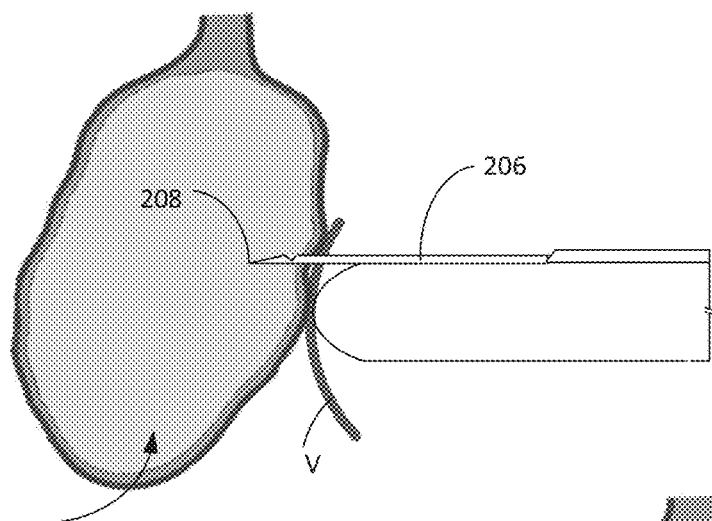
Figure 6H:
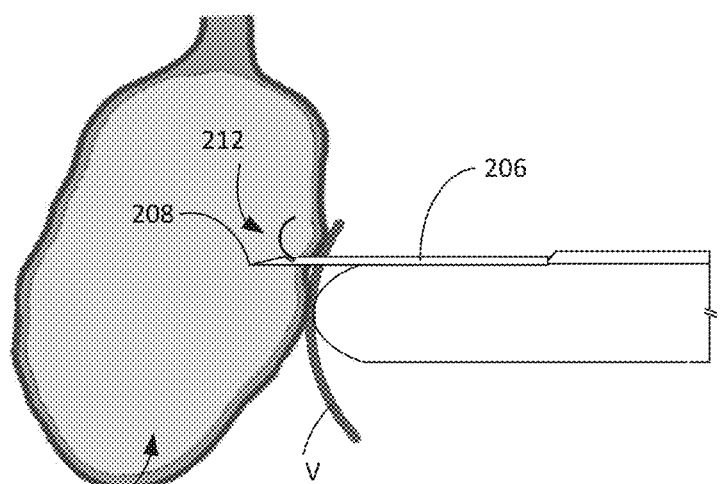

FIG. 6D illustrates elongated shaft 206 in a second orientation in the retracted state, while therapeutic portion 212 is re-deployed in FIG. 6E to perform another treatment. Energy is then delivered to this second treatment zone. Therapeutic portion 212 then may be retracted to the retracted state as shown in FIG. 6F. The distal region of therapeutic needle assembly 200 may be repositioned within ovary O or removed after completion of treatment for that ovary O. For example, as shown in FIG. 6G, elongated shaft 206 may be moved proximally in the retracted state along the same needle path without adjusting the angle of elongated shaft 206 via the single entry point for further energy delivery. Therapeutic portion 212 then is re-deployed in FIG. 6H to perform another treatment. Energy is then delivered to this third treatment zone. Therapeutic portion 212 is retracted again and therapeutic needle assembly 200 may be flipped to deliver energy in a fourth treatment zone. Additionally or alternatively, elongated shaft 200 may be moved proximally yet again in the retracted state to deliver further treatments. In this manner, multiple ablations may be achieved in each ovary, such as 4 ablations in a smaller ovary (as determined by the clinician from ultrasound imaging), 8 ablations in a larger ovary, or an amount of ablations sufficient to achieve the desired volume of ablated ovarian tissue, such as 1% to 25%, or more preferably, 5% to 10% of the total volume of the ovary.

Figure 6I:
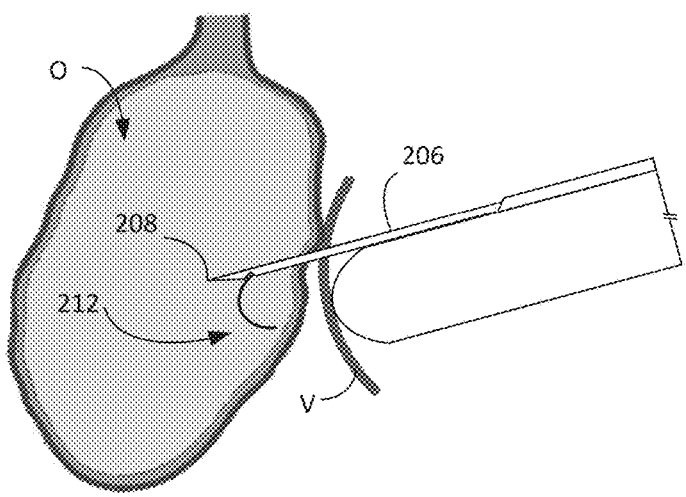

FIG. 6I illustrates yet another location ovary O can be treated using a single puncture of vaginal wall V and ovary O after retraction redeployment of therapeutic portion 212. In FIG. 6I, therapeutic needle assembly 200 is moved to a different angle along a different needle path via the same single puncture for optional further treatment(s). Creating fewer punctures and minimizing the amount of device manipulation may have several benefits including, but not limited to, reduced pain or discomfort by the patient due to less damage caused to the outside of the ovary and reducing the risk for adhesion formation (during the procedure or after the procedure), ease-of-use to the operator, reduced procedure time, and/or reduced chances of complications such as bleeding. In other examples, fewer or more treatments could be performed. Additionally or alternatively, multiple punctures could be performed in order to position the therapeutic element into the different zones for treatment. After the first ovary is treated, the second ovary may be treated in a similar manner.

The emission of energy into ovarian tissue (e.g., stroma) ablates the tissue to rebalance the ovary. For example, the ablation(s) is(are) expected to reduce hormonal imbalance between hormones such as the Follicle Stimulating Hormone (FSH) and the Luteinizing Hormone (LH), thereby treating a fertility condition such as Polycystic Ovary Syndrome (PCOS).

Figure 7:
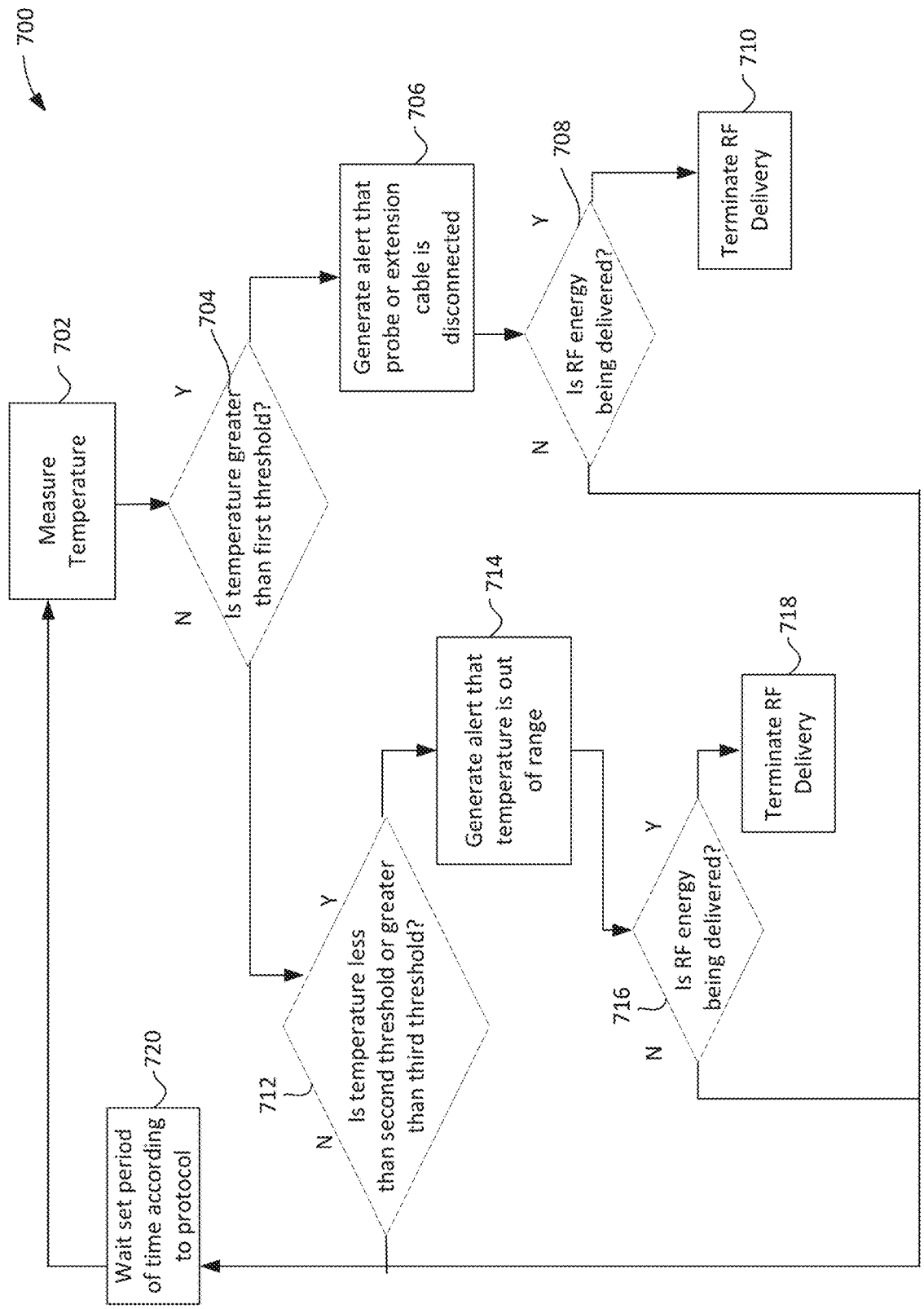
FIGS. 7-9 are flow charts illustrating exemplary methods for monitoring measured parameters in a system for performing an ovarian procedure.
Figure 8:
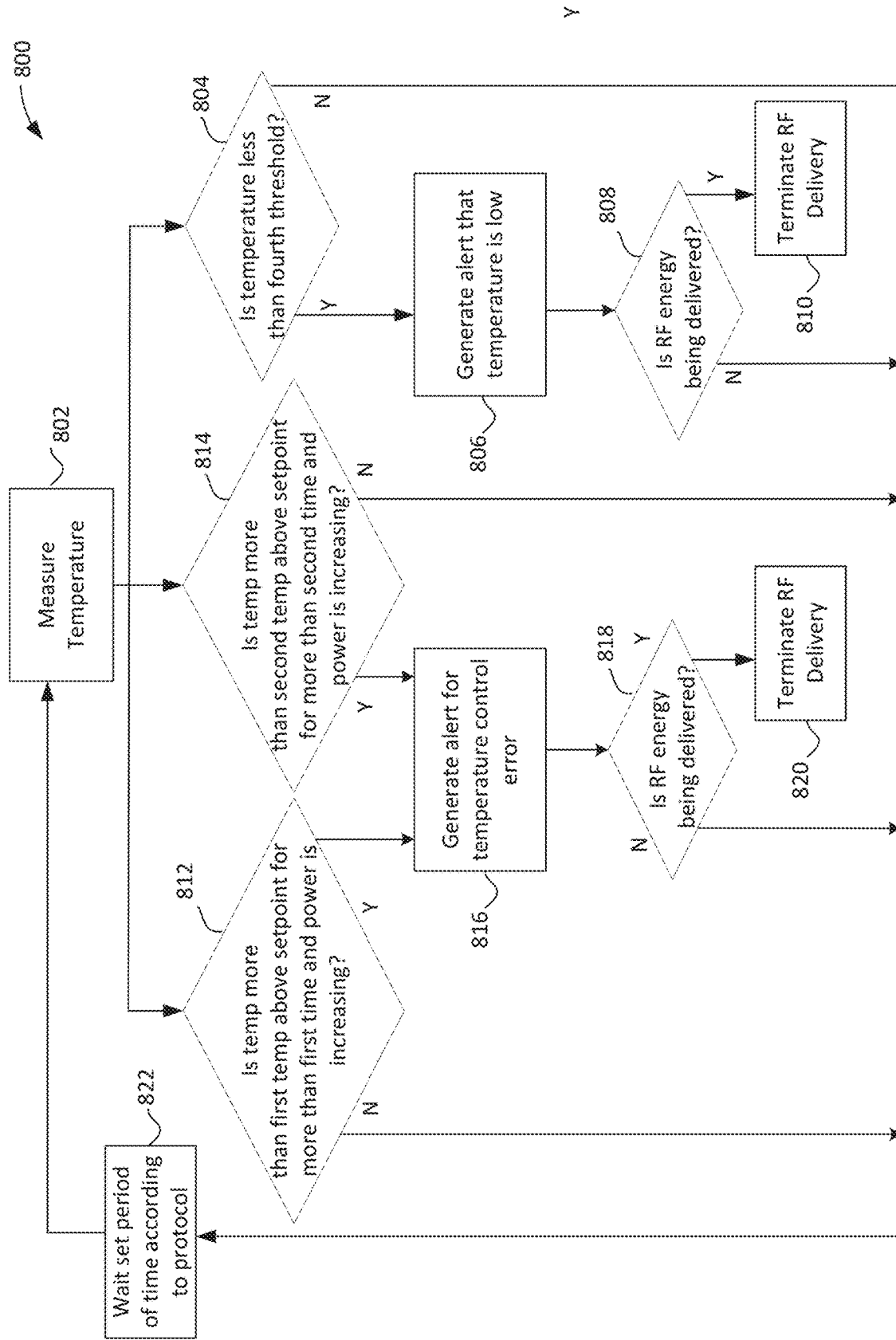
Figure 9:
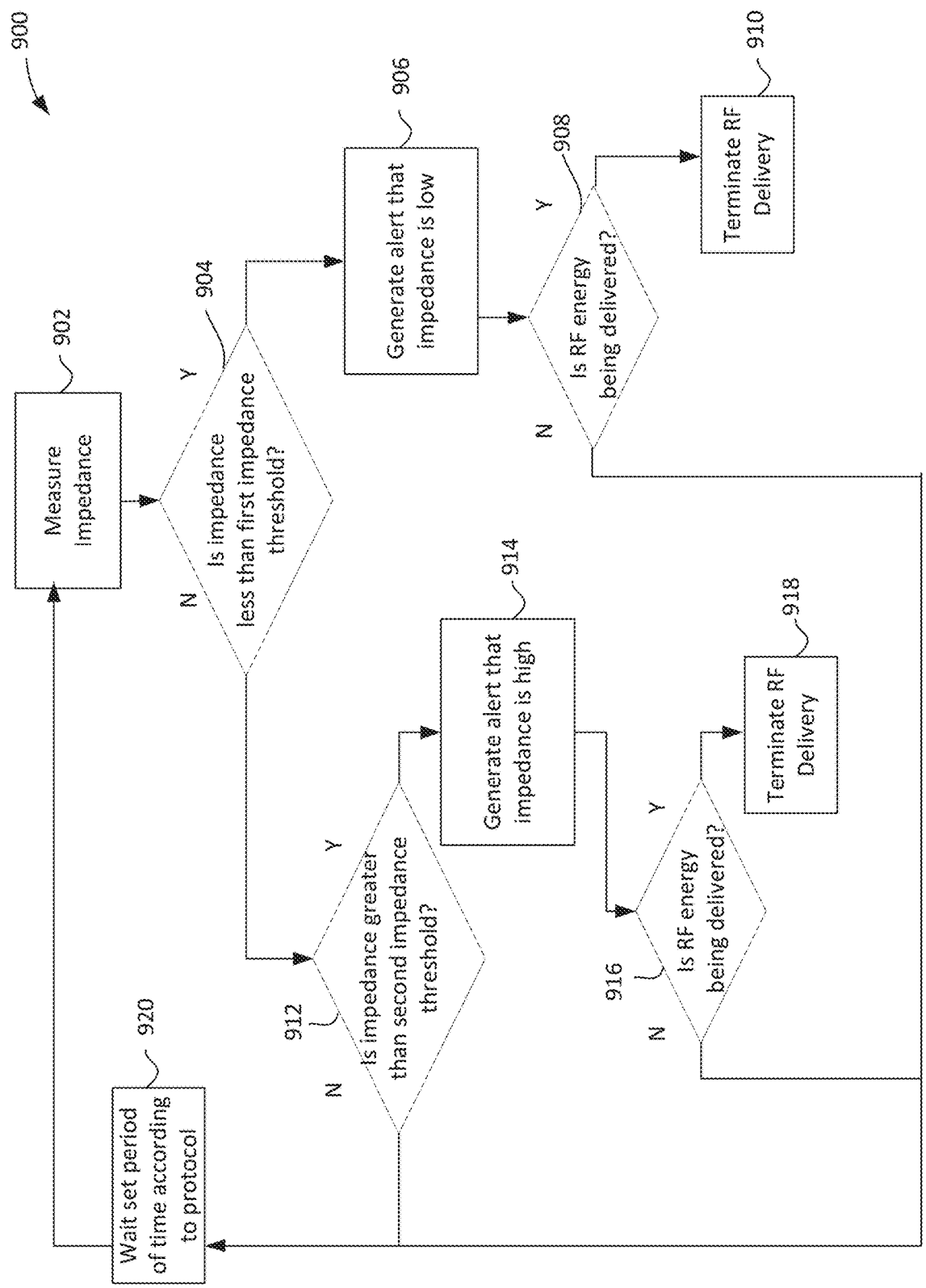

Referring now to FIGS. 7-9, methods for monitoring use of system 100 during an ovarian procedure are illustrated. System sensors 250 and/or conductive needle 252 may be used to measure temperature and/or impedance. For example, a temperature-sensing element could be coupled to each of first and second electrodes 246, 248. Furthermore, system sensors 250 and/or conductive needle 252 could also be used to detect if the device moves inappropriately during the treatment delivery. For example, device movement could be inferred by sensing sudden changes in temperature, impedance, and/or power. An increase in impedance could also signify changes in tissue characteristics such as collagen denaturization, dessication, or char formation.

A processor on the computer running generator software 500 (which may be generator 400 itself) may be operable to run algorithms based on these one or more measured system parameters. When implemented, an algorithm may be designed to modify a parameter of energy delivery. For example, system 100 may comprise an automated treatment delivery algorithm that automatically responds and adjusts and/or terminates treatment in response to parameters such as temperature, impedance, treatment duration, treatment power and/or system status. Additionally, system 100 may inform the user of monitored parameters and/or alarms. The alarm detection of the algorithm may include a routine for evaluating the data received from sensors 250 and/or conductive needle 252 and alerting abnormal conditions for the operator. The alert may be displayed on graphical user interface 410 as a numerical measurement, a wave form, text, a plot, a chart, a graph, or the like. Multiple sensed parameters may be displayed at one time and the displayed sensed parameters may be real-time measurements. Sensed parameters may be continuously received.

FIG. 7 is exemplary method 700 for measuring temperature (e.g., thermistor temperature) sensed by therapeutic needle assembly 200. At 702, one or more signals indicative of one or more sensed parameters, such as temperature, are received by generator 400 from sensors 250 and/or conductive needle 252. At 704, a processor on the computer running generator software 500 may run an algorithm stored in memory to determine if the temperature is above a first predetermined temperature threshold. At 706, if the temperature is above the first predetermined temperature threshold, an alert may be generated on graphical user interface 410 indicating that an event, e.g., the probe or extension cable is disconnected. In one embodiment, the first predetermined temperature threshold is within 115-125 degrees Celsius, for example, 120 degrees Celsius. At 708, the processor, via execution of the algorithm, determines whether energy is being delivered. If so, the processor causes termination of energy delivery at 710. If not, step 720 (described below) is executed.

If the measure temperature is not above the first predetermined temperature threshold, the processor, via execution of the algorithm, determines whether the temperature is below a second predetermined temperature threshold or above a third predetermined temperature threshold, at 712. In one embodiment, the second predetermined temperature threshold is within 5-15 degrees Celsius, for example, 10 degrees Celsius. The third predetermined temperature threshold may be, for example, within 40-50 degrees Celsius, such as 45 degrees Celsius. At 714, if the measured temperature is below the second predetermined temperature threshold or above the third predetermined temperature threshold, an alert may be generated on graphical user interface 410 indicating that the temperature is out of range. If not, step 720 (described below) is executed.

If the temperature is determined to be out of range, at 716, the processor, via execution of the algorithm, determines whether energy is being delivered. If so, the processor causes termination of energy delivery at 718. If, at 708 or 716 energy was not being delivered, the processor, via execution of the algorithm, may, at 720, wait a set period of time according to a protocol stored in the memory before returning to step 702 to measure temperature again. In this manner, temperature may be monitored throughout the course of using therapeutic needle assembly 200.

FIG. 8 is exemplary method 800 for measuring probe temperature. At 802, one or more signals indicative of one or more sensed parameters, such as temperature, are received by generator 400 from sensors 250 and/or conductive needle 252. At 804, a processor on the computer running generator software 500 may run an algorithm to determine if the temperature is below a fourth predetermined temperature threshold. In one embodiment, the fourth predetermined temperature threshold is within 15-25 degrees Celsius, for example, 20 degrees Celsius. At 806, if the temperature is below the fourth predetermined temperature threshold, an alert may be generated on graphical user interface 410 indicating an event, e.g., that probe temperature is low. If the temperature is determined to be less than the fourth predetermined threshold, at 808, the processor, via execution of the algorithm, determines whether energy is being delivered. If so, the processor causes termination of energy delivery at 810. If the temperature was not below the fourth predetermined temperature threshold, the processor, via execution of the algorithm, at 812 determines whether the temperature is more than a first temperature (e.g., 5 degrees Celsius) above a temperature setpoint for more than a first period of time (e.g., 5 seconds) while power is increasing. At 816, if the measured temperature exceeds the thresholds for the measured time, an alert will generate on graphical user interface 410 indicating temperature control error. For example, if the measured probe temperature is 5 degrees Celsius above the temperature setpoint stored in memory for 5 seconds or more, the alert may be generated. If so, at 818, the processor, via execution of the algorithm, determines whether energy is being delivered. If so, the processor causes termination of energy delivery at 820.

If the temperature was not below the fourth predetermined temperature threshold, the processor, via execution of the algorithm, at 814 determines whether the temperature is more than a second temperature (e.g., 10 degrees Celsius) above the temperature setpoint for more than a second period of time (e.g., 1 seconds) while power is increasing. In this example, the second temperature is greater than the first temperature and the second period of time is less than the first period of time. In this manner, if temperature is too high (e.g., above the second temperature), corrective action may be taken more immediately. Steps 816-820 may be repeated, following the determination at 814, that the temperature is more than the second temperature above the temperature setpoint for more than the second period of time while power is increasing. If, at 808 or 818, energy was not being delivered, or at 804, 814, or 812 the thresholds were not met, the processor, via execution of the algorithm, may, at 822, wait a set period of time according to a protocol stored in the memory before returning to step 802 to measure temperature again. In this manner, probe temperature may be monitored throughout the course of using therapeutic needle assembly 200.

FIG. 9 is exemplary method 900 for measuring impedance. At 902, one or more signals indicative of one or more sensed parameters, such as impedance, are received by generator 400 from system sensors 250 and/or conductive needle 252. At 904, a processor on the computer running generator software 500 may run an algorithm to determine if impedance measures below a first predetermined impedance threshold. In one example, the first predetermined impedance threshold is within 40-60 ohms, for example, 50 ohms. At 906, if the impedance is below the first predetermined impedance threshold, an alert may be generated on graphical user interface 410 indicating impedance is low. At 908, the processor, via execution of the algorithm, determines whether energy was being delivered. If so, the processor causes termination of energy delivery at 910. If the impedance was not below the first predetermined impedance threshold, the processor, via execution of the algorithm, at 912 determines whether the measured impedance is above a second predetermined impedance threshold. In one embodiment, the second predetermined impedance threshold is within 900-1100 ohms, for example, 1000 ohms. At 914, if the measured impedance is above the second predetermined impedance, an alert may be generated on graphical user interface 410 indicating impedance is high. At 916, the processor, via execution of the algorithm, determines whether energy was being delivered. If so, the processor causes termination of energy delivery at 918. If, at 908 or 916 energy was not being delivered, the processor, via execution of the algorithm, may, at 920, wait a set period of time according to a protocol stored in the memory before returning to step 902 to measure impedance again. In this manner, impedance at the treatment area may be monitored throughout the course of using therapeutic needle assembly 200.

FIGS. 10-13 illustrate graphical user interface 410 designed to communicate with processor of generator 400. The exemplary screen shots generated by graphical user interface 410 show graphical interpretations of the data received from sensors 250 and/or conductive needle 252. Graphical user interface 410 is designed to display measured parameters such as temperature, impedance, power, and the corresponding alerts, as well as information input by the clinician/operator. Graphical user interface 410 is designed to present that information in an intuitive, easily understood format for operator review such as numbers, wave forms, text, a plot, a chart, a graph, or the like. Graphical user interface 410 may include buttons for receiving user input, such as patient/procedure related information, ovarian volume, powering the device, and clearing alerts.

Figure 10:
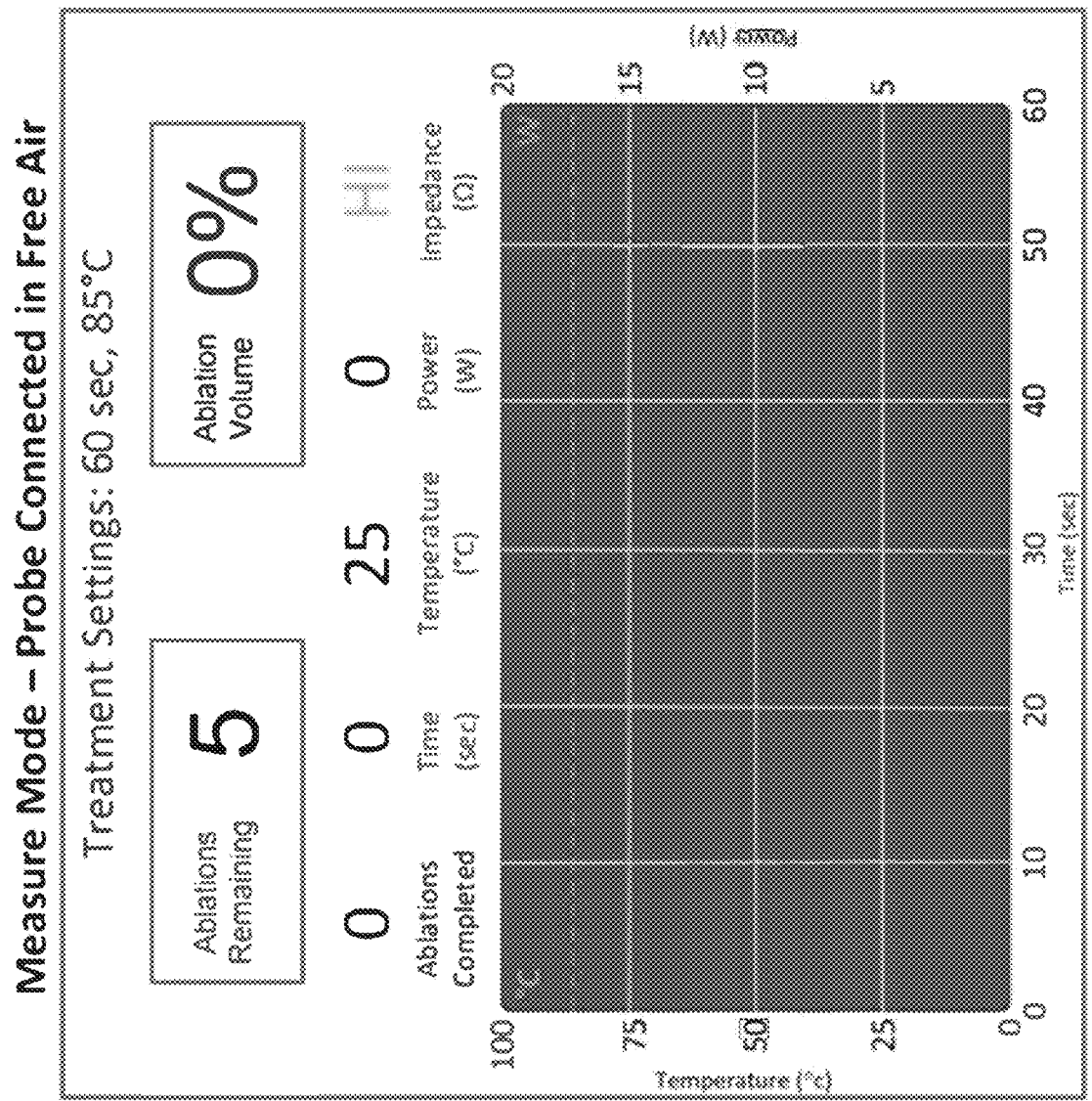
Figure 11:
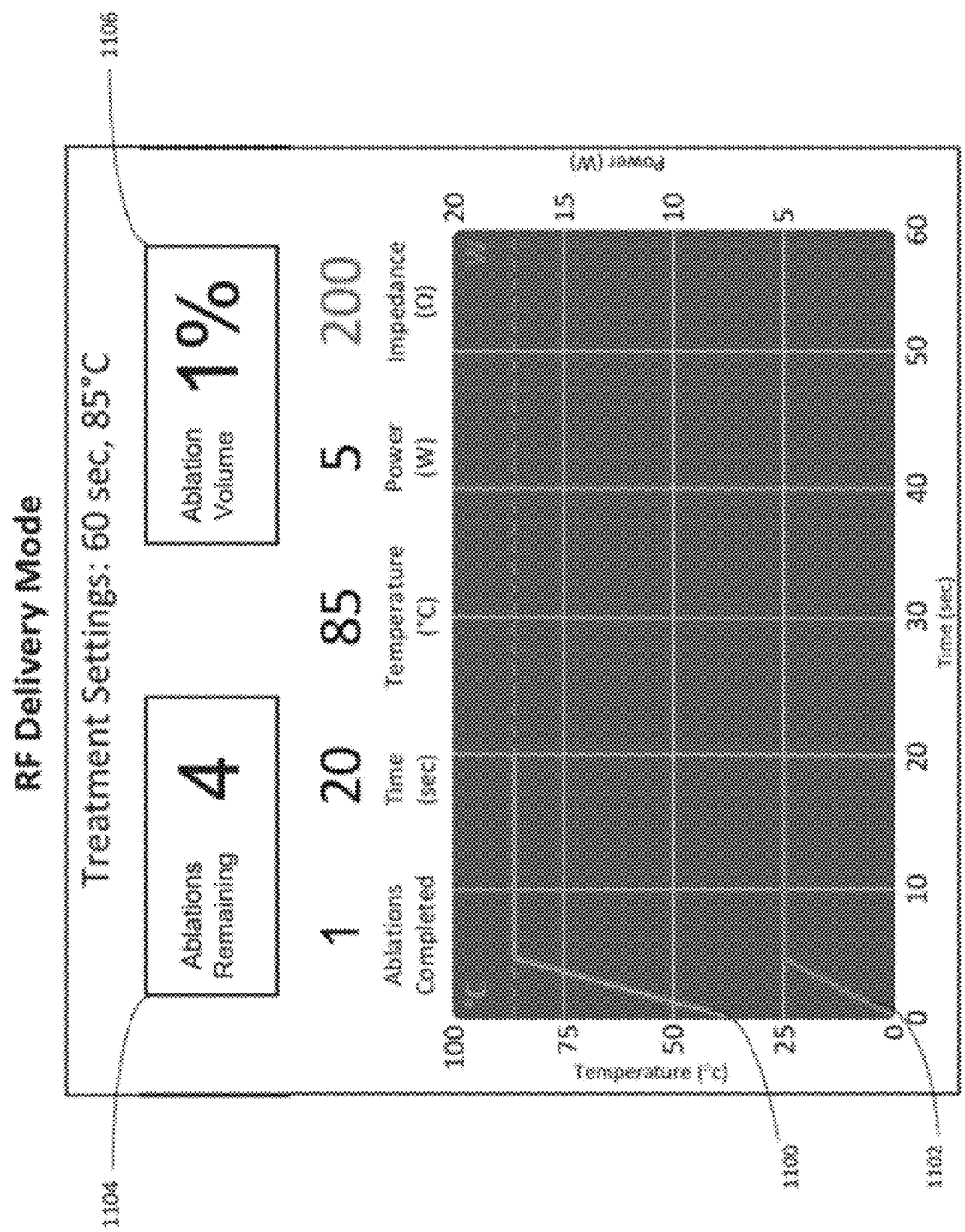
Figure 12:
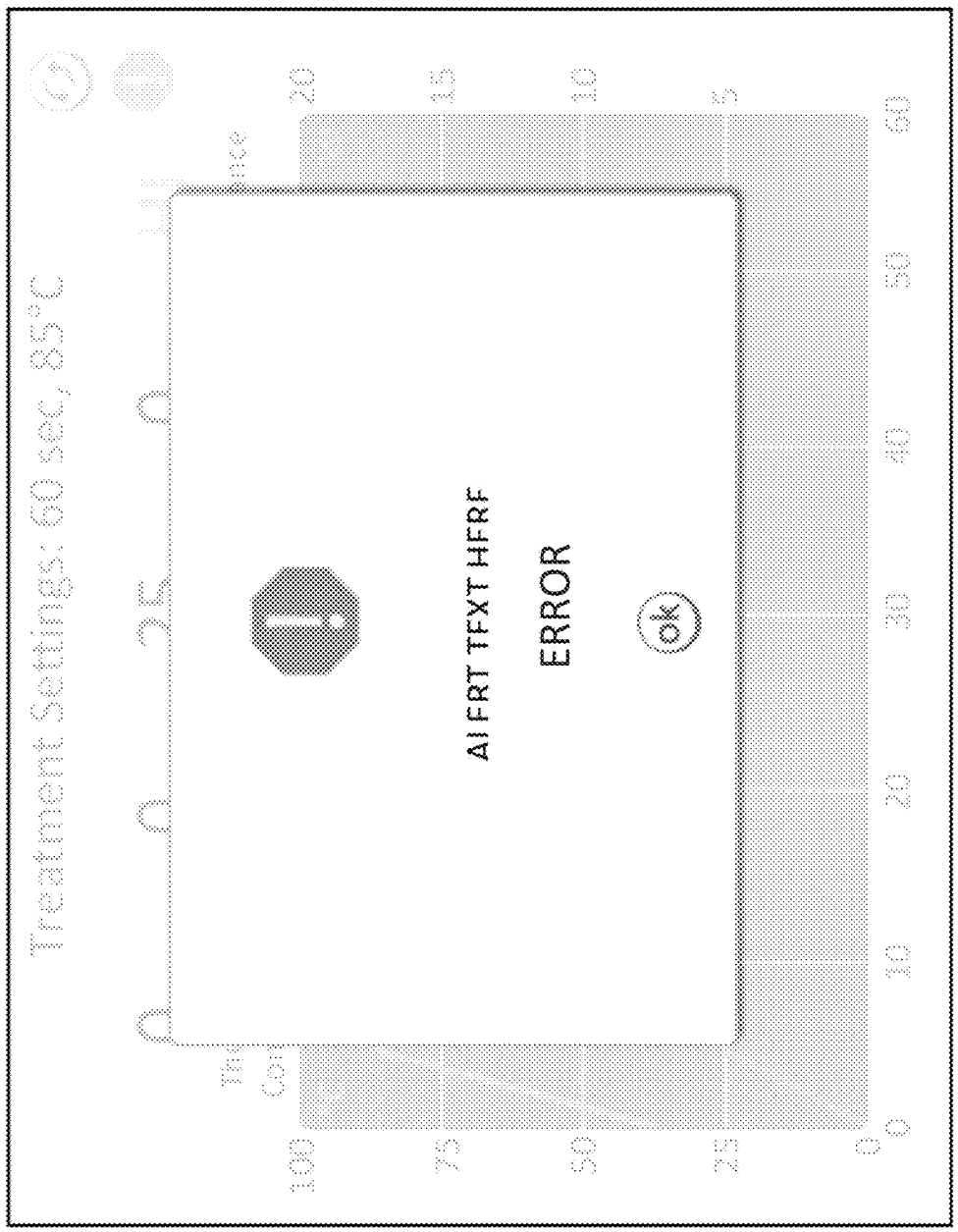

FIG. 10 depicts an exemplary measure mode screen prior to energy delivery. Sensors 250 and/or conductive needle 252 may be used before treatment is applied to characterize or map the target tissue; for instance, impedance measures could be used to sense if the ultrasound probe is properly positioned for treatment. FIG. 11 depicts exemplary temperature 1100, power reading 1102, ablations remaining 1104, and ablation volume 1106. As the tissue heats and changes its characteristics, temperature may also increase. Sensors 250 and/or conductive needles 252 could also be used during treatment to dynamically adjust treatment parameters. As exemplified in FIG. 12, treatment termination may also occur and result in an error message in the event that certain conditions are met, as described in FIGS. 7-9. FIG. 13 depicts a table providing for selection of ablation parameters for a given number of ablations and desired ablation volume.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed:

1. A system for performing an ovarian procedure, the system configured for use with an ultrasound probe, the system comprising:
    a therapeutic needle assembly comprising a proximal region and a distal region, the therapeutic needle assembly further comprising:
        an elongated shaft at the distal region, the elongated shaft comprising a lumen, a port, and a needle tip at a distal end of the elongated shaft, the needle tip configured to pierce a vaginal wall and pierce an ovarian wall for placement of the port into an ovary;
        a therapeutic portion disposed within the lumen of the elongated shaft in a retracted state, the therapeutic portion comprising a distal tip and a plurality of electrodes configured to be deployed to extend out the port of the elongated shaft in a deployed state, at least one of the plurality of electrodes configured to emit energy into ovarian tissue of the ovary while in the deployed state;
        a conductive needle extending through the plurality of electrodes of the therapeutic portion and forming the distal tip of the therapeutic portion, the conductive needle configured to sense electrical activity;
        a handle at the proximal region, the handle comprising an actuator configured to transition the therapeutic portion between the retracted state and the deployed state when actuated; and
        a lubricant tube disposed within the lumen of the elongated shaft adjacent to the port of the elongated shaft, wherein the therapeutic portion is configured to transition from the retracted state by moving within the lumen, through the lubricant tube, and out the port to the deployed state responsive to actuation at the actuator and to be retracted into the port and into the lumen using the lubricant tube without damaging the plurality of electrodes,
        wherein the elongated shaft comprises an angled interface at the lumen's distal end at the port to guide the therapeutic portion to exit the lumen of the elongated shaft out the port at an angle to, together with the lubricant tube, facilitate in positioning the therapeutic portion for treatment; and
    a generator operatively coupled to the therapeutic portion and the conductive needle to receive electrical signals indicative of impedance from the conductive needle, the generator configured to process the electrical signals indicative of impedance and to cause at least one of the plurality electrodes of the therapeutic portion in the deployed state to emit the energy into the ovarian tissue of the ovary based on the processed electrical signals indicative of impedance.

2. The system of claim 1, wherein the needle tip is cored to define a cavity to facilitate piercing the vaginal wall and the ovarian wall.

3. The system of claim 1, further comprising an adapter comprising a needle assembly interface and an ultrasound probe interface, the ultrasound probe interface configured to be removably coupled to the ultrasound probe, the needle assembly interface configured to be removably coupled to an adapter interface of the handle such that the therapeutic needle assembly is coupled to the ultrasound probe.

4. The system of claim 3, wherein the adapter interface and the needle assembly interface are configured to permit reorientation of the therapeutic needle assembly relative to the adapter between a first orientation and a second orientation.

5. The system of claim 4, wherein the adapter interface of the handle and the needle assembly interface are configured to lock together in the first orientation and permit reorientation of the therapeutic needle assembly relative to the adapter such that the adapter interface of the handle and the needle assembly interface are configured to lock together in the second orientation.

6. The system of claim 5, wherein the adapter interface of the handle comprises first and second notches on opposing surfaces of the handle, the first and second notches configured to contact opposing surfaces of the needle assembly interface to lock the adapter interface of the handle to the needle assembly interface in the first orientation and the second orientation.

7. The system of claim 3, wherein the adapter ensures alignment of the therapeutic portion within a field-of-view of the ultrasound probe.

8. The system of claim 3, further comprising a needle guide configured to be removably coupled to the ultrasound probe and to receive the elongated shaft therethrough to stabilize the elongated shaft during a procedure,
    wherein at least one of the therapeutic needle assembly and the needle guide or the needle guide and the adapter are formed as a single entity.

9. The system of claim 1, wherein the generator comprises a processor configured to execute instructions stored on a non-transitory computer readable medium to instruct the generator to modify delivery of energy to the therapeutic portion if measured data indicates that at least one measured parameter is outside of a predetermined range.

10. The system of claim 1, wherein the therapeutic portion comprises at least one sensor configured to generate data during emission of energy from the therapeutic portion.

11. The system of claim 10, wherein the generator comprises a processor in electrical communication with the at least one sensor, the processor configured to execute instructions stored on a non-transitory computer readable medium to: receive the data from the at least one sensor; determine whether the data is within a predetermined range; and instruct the generator to modify delivery of energy to the therapeutic portion if the data indicates that at least one measured parameter is outside of the predetermined range.

12. The system of claim 11, wherein the processor is configured to run a routine to cause generation of an alert on a graphical user interface if the data is above a first predetermined threshold or below a second predetermined threshold.

13. The system of claim 10, wherein the at least one sensor comprises at least one temperature sensor configured to measure temperature at at least one of the plurality of electrodes or probe temperature or both.

14. The system of claim 10, further comprising a graphical user interface configured to display information indicative of a treatment process based on data from the at least one sensor.

15. The system of claim 1, further comprising a graphical user interface configured to display information indicative of at least one of: ovarian volume per ovary, ovarian volume per patient, recommended ablation parameters, set ablation parameters, power settings, recommended number of ablations, required number of ablations, recommended volume of ovarian ablation, required volume of ovarian ablations, number of completed ablations, number of remaining ablations, percentage of ovarian volume ablated, or percentage of ovarian volume remaining to be ablated.

16. The system of claim 15, wherein the information indicative of recommended ablation parameters or set ablation parameters is displayed in a table.

17. The system of claim 15, wherein the information displayed is updated after an ablation procedure.

18. The system of claim 15, further comprising a processor configured to execute instructions stored on a non-transitory computer readable medium to receive input data indicative of ovarian volume, wherein the information displayed on the graphical user interface is based at least in part on the input data indicative of ovarian volume.

19. The system of claim 1, wherein the therapeutic portion is configured to form a curve in the deployed state.

20. The system of claim 1, wherein the plurality of electrodes are cuff electrodes.

21. The system of claim 1, wherein the plurality of electrodes comprise an active electrode and a return electrode, the active electrode configured to emit continuous or pulsed radiofrequency energy.

22. The system of claim 1, wherein the therapeutic portion is configured to emit the energy into the ovarian tissue to treat polycystic ovary syndrome (PCOS).

23. The system of claim 1, wherein the lubricious tube comprises a polymer biocompatible material comprising at least one of ultra-high-molecular-weight polyethylene or fluoropolymers.

24. The system of claim 1, wherein the system is configured for use with a vaginal ultrasound probe.

25. The system of claim 1, wherein the generator is configured to modify delivery of energy to at least one of the plurality of electrodes of the therapeutic portion if the information indicates that a measured impedance is outside of a predetermined range.

26. The system of claim 25, wherein the generator automatically terminates delivery of energy if the information indicates that the measured impedance is outside of the predetermined range.

* * * * *